ID#

United States Patent
Izuhara et al.

(10) Patent No.: US 9,625,451 B2
(45) Date of Patent: Apr. 18, 2017

(54) METHOD FOR DIAGNOSING CHRONIC SINUSITIS

(71) Applicants: SAGA UNIVERSITY, Saga-shi, Saga (JP); YAMAGATA UNIVERSITY, Yamagata-shi, Yamagata (JP)

(72) Inventors: Kenji Izuhara, Saga (JP); Shoichiro Ohta, Saga (JP); Kazuhiko Arima, Saga (JP); Hiroshi Shiraishi, Saga (JP); Shoichi Suzuki, Saga (JP); Nobuo Ohta, Yamagata (JP); Akihiro Ishida, Yamagata (JP); Yusuke Suzuki, Yamagata (JP)

(73) Assignees: SAGA UNIVERSITY, Saga-Shi (JP); YAMAGATA UNIVERSITY, Yamagata-Shi (JP)

( * ) Notice: Subject to any disclaimer, the term of this patent is extended or adjusted under 35 U.S.C. 154(b) by 65 days.

(21) Appl. No.: 14/354,355

(22) PCT Filed: Oct. 30, 2012

(86) PCT No.: PCT/JP2012/078008
§ 371 (c)(1),
(2) Date: Apr. 25, 2014

(87) PCT Pub. No.: WO2013/065671
PCT Pub. Date: May 10, 2013

(65) Prior Publication Data
US 2014/0273280 A1   Sep. 18, 2014

(30) Foreign Application Priority Data
Oct. 31, 2011  (JP) .................... 2011-238913

(51) Int. Cl.
*G01N 33/53* (2006.01)
*G01N 33/68* (2006.01)

(52) U.S. Cl.
CPC ..... *G01N 33/5308* (2013.01); *G01N 33/6893* (2013.01); *G01N 2800/14* (2013.01); *G01N 2800/7095* (2013.01)

(58) Field of Classification Search
None
See application file for complete search history.

(56) References Cited

U.S. PATENT DOCUMENTS

| | | | |
|---|---|---|---|
| 2003/0073137 A1* | 4/2003 | Chen ................... | C07K 14/475 435/7.5 |
| 2003/0152956 A1 | 8/2003 | Ohtani et al. | |
| 2006/0051324 A1* | 3/2006 | Kirkin ................ | A61K 39/0011 424/93.7 |
| 2009/0035314 A1* | 2/2009 | Kim ...................... | A61K 38/17 424/141.1 |
| 2010/0138937 A1 | 6/2010 | Urade et al. | |
| 2011/0086360 A1 | 4/2011 | Izuhara et al. | |
| 2012/0219977 A1* | 8/2012 | Garnero et al. ............. | 435/7.93 |

FOREIGN PATENT DOCUMENTS

| | | | |
|---|---|---|---|
| JP | 2005-500059 A | 1/2005 | |
| JP | 2010-96748 A | 4/2010 | |
| JP | 2010-145294 A | 7/2010 | |
| WO | WO 02/052006 A1 | 7/2002 | |
| WO | WO 03/016471 A2 | 2/2003 | |
| WO | WO 2006/123677 A1 | 11/2006 | |
| WO | WO 2009075883 A2 * | 6/2009 | ....... G01N 33/57484 |
| WO | WO 2009/092052 A2 | 7/2009 | |
| WO | WO 2009/148184 A1 | 12/2009 | |
| WO | WO 2009148184 A1 * | 12/2009 | ........... C12Q 1/6883 |
| WO | WO 2010139768 A1 * | 12/2010 | |

OTHER PUBLICATIONS

Sasaki et al., Elevated serum periostin levels in patients with bone metastases from breast but no lung cancer., 77, (2003), p. 245-25.*
Ishida et al., Expression of Pendrin and Periostin in Allergic Rhinitis and Chronic Rhinosinusitis, Allergology International, 61, (2012), p. 589-595.*
Kramer et al., "Nasal Interleukin-5, Immunoglobulin E, Eosinophilic Cationic Protein, and Soluble Intercellular Adhesion Molecule-1 in Chronic Sinusitis, Allergic Rhinitis, and Nasal Polyposis," Laryngoscope (2000), vol. 110, pp. 1056-1062.
Matsune et al., "Preliminary Study of Vascular Endothelial Growth Factor in Rhinosinusitis," Jibi Meneki Allergy (Otological Immunological Allergy) (1999), vol. 17, No. 1, pp. 12-16, with partial English translation.
Stankovic et al., "Gene Expression Profiling of Nasal Polyps Associated With Chronic Sinusitis and Aspirin-Sensitive Asthma," Laryngoscope (May 2008), vol. 118, pp. 881-889.
Takayama et al., "Periostin: A novel component of subepithelial fibrosis of bronchial asthma downstream of IL-4 and IL-13 signals," J. Allergy Clin. Immunol. (2006), vol. 118, pp. 98-104.
Ben et al., "Circulating levels of periostin may help identify patients with more aggressive colorectal cancer," International Journal of Oncology (2009), vol. 34, pp. 821-828.
Daines et al., "Periostin and osteopontin are overexpressed in chronically inflamed sinuses," Int. Forum Allergy Rhinol. (Mar./Apr. 2011), vol. 1, No. 2, pp. 101-105.
Gordon et al., "A protective role for periostin and TGF-β in IgE-mediated allergy and airway hyperresponsiveness," Clinical & Experimental Allergy (2012), vol. 42, pp. 144-155.
Kanno et al., "Periostin, secreted from stromal cells, has biphasic effect on cell migration and correlates with the epithelial to mesenchymal transition of human pancreatic cancer cells," Int. J. Cancer (2008), vol. 122, pp. 2707-2718.
Kern et al., "Diagnosis and treatment of chronic rhinosinusitis: focus on intranasal Amphotericin B," Therapeutics and Clinical Risk Management (2007), vol. 3, No. 2, pp. 319-325.

* cited by examiner

*Primary Examiner* — Christine Foster
*Assistant Examiner* — Ellen J Marcsisin
(74) *Attorney, Agent, or Firm* — Birch, Stewart, Kolasch & Birch, LLP

(57) ABSTRACT

The present invention provides a method for detecting chronic sinusitis, which comprises measuring the concentration of a periostin protein in blood or nasal secretion collected from a test subject. Thereby, a method for detecting chronic sinusitis, which is capable of detecting chronic sinusitis more simply, more promptly and less invasively, is provided.

10 Claims, 9 Drawing Sheets

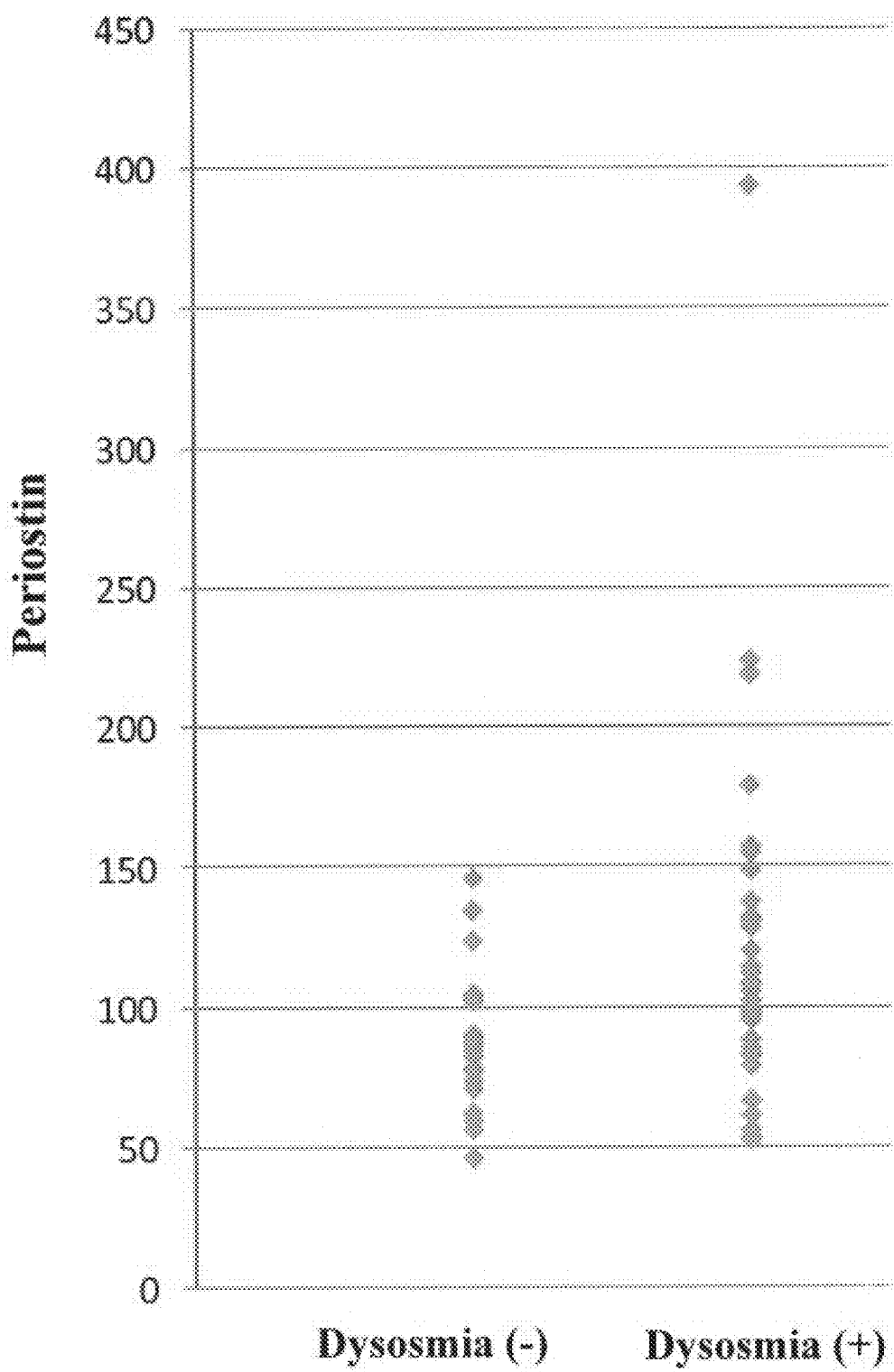

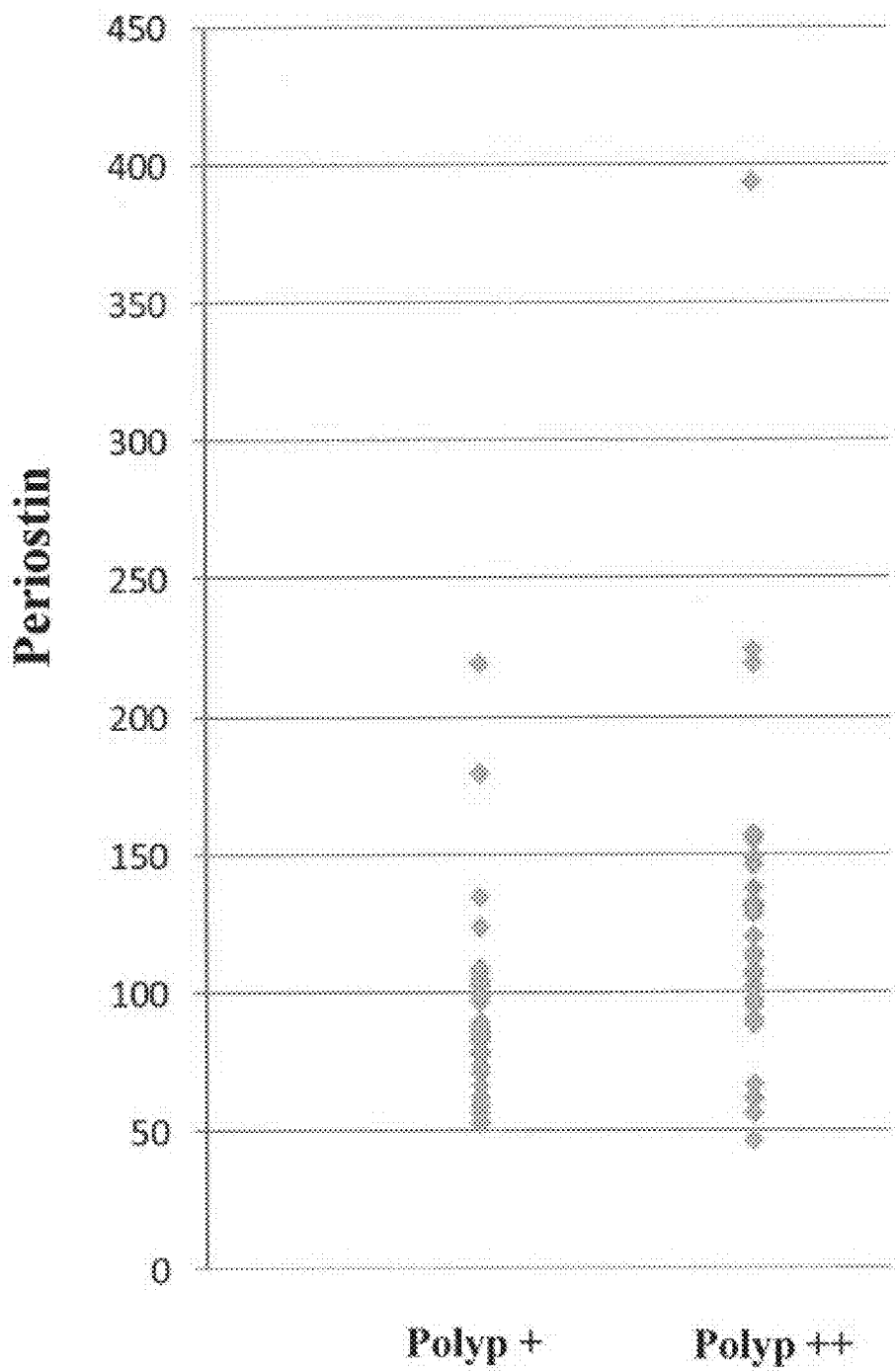

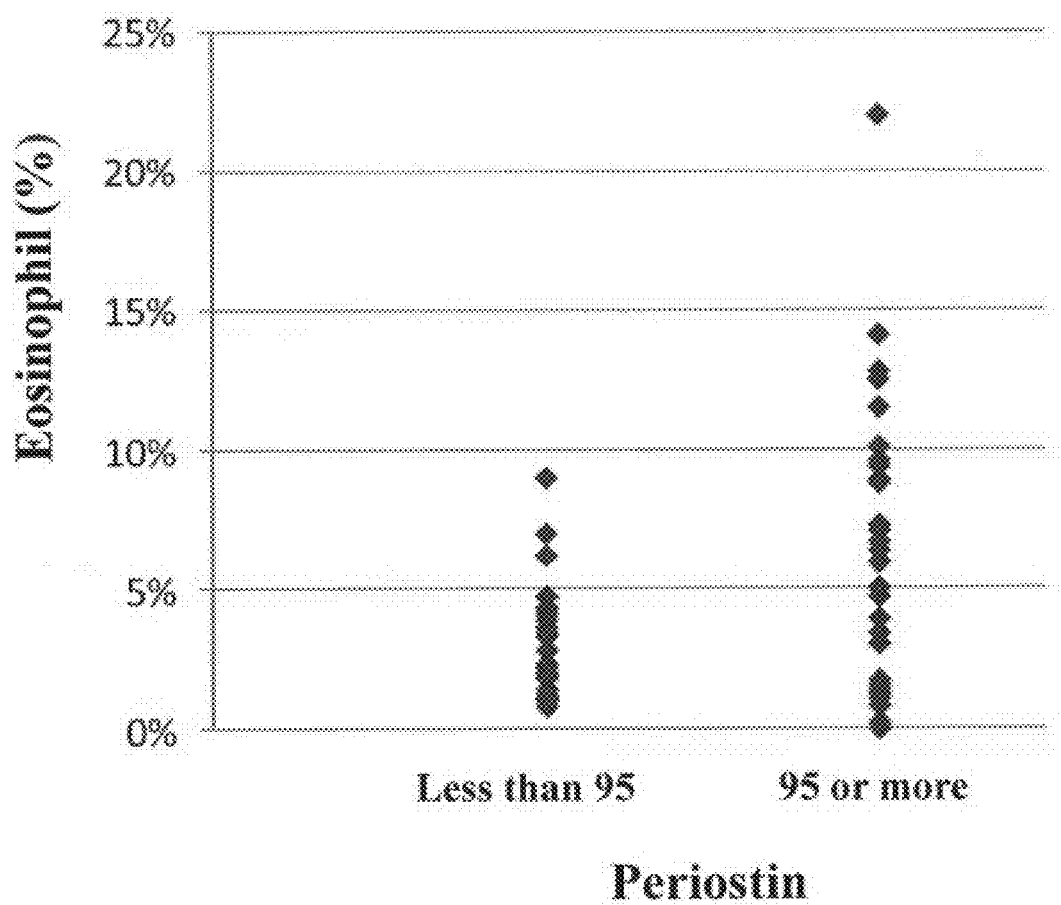

METHOD FOR DIAGNOSING CHRONIC SINUSITIS

TECHNICAL FIELD

The present invention relates to a method for detecting chronic sinusitis, a method for analyzing a biological sample associated with the aforementioned detection method, and the like.

BACKGROUND ART

Chronic sinusitis is a disease in which a natural orifice is closed due to the swelling of the mucous membrane by inflammation of paranasal sinuses and the storage of mucus in the sinus or generation of polypoid tissues (nasal polyps) in the nasal cavity occurs, thereby causing clinical symptoms such as nasal discharge, nasal obstruction, postnasal drip, and dull headache. Chronic sinusitis is caused by various factors, and it is considered that this disease is influenced by bacterial or viral infection, allergic reaction, genetic factors, living environment, etc. Methods for treating chronic sinusitis include administration of antibiotics and various types of surgical treatments.

Allergic rhinitis caused by various types of allergic reactions has symptoms similar to those of chronic sinusitis. Thus, it is difficult to distinguish allergic rhinitis from chronic sinusitis based on subjective findings. Since administration of antiallergic agents is effective for the treatment of allergic rhinitis, it is desirable to easily distinguish the two diseases and to perform suitable treatments on both of them.

However, to date, endoscopy or radiographic examination has been generally performed on tissues in the nasal cavity as a method for diagnosing chronic sinusitis. Since these diagnostic methods have required examination and evaluation performed by medical specialists, these methods have not necessarily been simple, and great burdens have been placed on patients.

Recently, chronic sinusitis has also been diagnosed by observing surgical specimens or nasal polyp tissues in inflammatory sites under a microscope. This diagnostic method utilizes the phenomenon in which inflammation-related substances generated as a result of infiltration of neutrophils, eosinophils and the like, such as cytokines, growth factors, adhesion molecules, and inflammatory substances, are increased in the inflammatory sites of chronic sinusitis. This method makes a diagnosis of chronic sinusitis based on the presence or absence of these substances, or the density of these substances. For instance, Patent Literature 1 discloses a method for diagnosing the severity of chronic sinusitis by measuring the expression of a hematopoietic prostaglandin D synthase (H-PDGS) protein or the amount of prostaglandin $D_2$ ($PDG_2$) in inflammatory sites based on tissue observation. The present inventors have also studied the expression of pendrin and periostin proteins in surgical specimens, and as a result, they have reported that it is possible to distinguish chronic sinusitis from allergic rhinitis based on an increase in the expression of pendrin and periostin in the inflammatory sites of chronic sinusitis or allergic rhinitis, so as to make a diagnosis (Non Patent Literature 1).

However, the aforementioned diagnosis, which uses an inflammation-related substance in a surgical specimen or the like as a marker, is also attended with complications such as limited facilities in which the diagnosis can be carried out, the long period of time required for obtaining results, invasiveness for patients upon collection of nasal tissues and the like. Thus, it has been desired to develop a novel tool, which improves the accuracy of diagnoses by medical specialists according to a more simple method, and which also enables the accurate diagnosis of chronic sinusitis even by non-specialists.

CITATION LIST

Patent Literature

[Patent Literature 1] WO2006/123677
[Patent Literature 2] WO2002/052006
[Patent Literature 3] WO2009/148184
[Patent Literature 4] JP Patent Publication (Kokai) No. 2010-096748 A
[Patent Literature 5] JP Patent Publication (Kokai) No. 2010-145294 A

Non Patent Literature

[Non Patent Literature 1] Akihiro ISHIDA et al., *Nippon Jibiinkoka Gukkai Kaiho* (Proceedings of the Oto-Rhino-Laryngological Society of Japan, Inc.) (2010 Apr. 20) Vol. 113, No. 4, Page 404
[Non Patent Literature 2] Kramer et al., Laryngoscope, Vol. 110, Pages 1056-1062, 2000
[Non Patent Literature 3] Shoji MATSUNE et al., *Jibi Meneki Allergy* (Otological Immunological Allergy) (1999) Vol. 17, No. 1, Pages 12-16
[Non Patent Literature 4] G. Takayama et al., J Allergy Clin Immunol, Vol. 118, Pages 98-104, 2006
[Non Patent Literature 5] Osamu SHIONO et al., *Jibiinkoka Meneki Allergy* (Otolaryngology Immunological Allergy) (2009) Vol. 27, No. 2, CD-ROM Page ROMBUN-NO.OP-11
[Non Patent Literature 6] Akihiro ISHIDA et al., Allergy (2009 Sep. 30) Vol. 58, No. 8/9, page 1219
[Non Patent Literature 7] Osamu SHIONO et al., Programs/Abstracts of the Japan society of Immunology & Allergology in Otolaryngology (2009) Vol. 27, page 80
[Non Patent Literature 8] Osamu SHIONO et al., *Jibiinkoka Meneki Allergy* (Otolaryngology Immunological Allergy) (2008) Vol. 26, No. 2, CD-ROM Page ROMBUNNO, 44
[Non Patent Literature 9] Osamu SHIONO et al., Proceedings of the Japanese Rhinologic Society (2008 Aug. 31) Vol. 47, No. 3, Page 235
[Non Patent Literature 10] Osamu SHIONO et al., Programs/Abstracts of the Japan society of Immunology & Allergology in Otolaryngology (2008) Vol. 26, Page 74

SUMMARY OF INVENTION

Technical Problem

With the aforementioned necessity as a backdrop, in recent years, attention has been focused on inflammation-related substances generated in inflammatory sites, which are secreted from the inflammatory sites into body fluids such as blood, and attempts have been made to diagnose chronic sinusitis based on the presence of such inflammation-related substances. However, inflammation-related substances observed in inflammatory sites are not necessarily secreted into body fluids such as blood, and thus, it is difficult to diagnose chronic sinusitis by measuring an inflammation-related substance in blood or the like.

That is to say, for example, Non Patent Literature 2 reports that, with regard to the concentration of inflammation-related substances in the sinus secretion of patients with chronic sinusitis, the concentration of ICAM-1 in the patents tends to be higher than that in healthy subjects, but in terms of IL-5 and ECP, no such difference from healthy subjects has been found. In addition, in terms of ICAM-1 as well, not all chronic sinusitis patients can be distinguished from healthy subjects or allergic rhinitis patients. Moreover, in Non Patent Literature 3 as well, the diagnosis of chronic sinusitis has been studied by measuring an inflammation-related substance using blood or the like. However, the diagnosis of chronic sinusitis has not yet been successfully completed.

Under the aforementioned circumstances, it is an object of the present invention to provide a method for detecting chronic sinusitis more simply, more promptly, and less invasively.

Solution to Problem

The present inventors have conducted intensive studies directed towards achieving the aforementioned object. As a result, the inventors have found that the concentration of a periostin protein is high in a biological sample derived from chronic sinusitis patients, such as blood of nasal secretion, and that the concentration of a periostin protein in blood or nasal secretion collected from the patient can be analyzed to obtain an analytical value that is useful when chronic sinusitis is diagnosed or detected more simply, more promptly, and less invasively, thereby completing the present invention.

Specifically, the present invention provides the following detection method, detection agent, and the like.

[1] A method for detecting or diagnosing chronic sinusitis, which comprises measuring the concentration of a periostin protein in blood or nasal secretion collected from a text subject.

[2] The method according to [1] above, which comprises determining that the text subject is suspected of having onset of chronic sinusitis, when the measured protein concentration in serum is 95 ng/mL or more.

[3] The method according to [1] above, which comprises determining that the test subject is suspected of having onset of chronic sinusitis, when the measured protein concentration in nasal lavage fluid is 0.8 ng/mL or more.

[4] The method according to [1] above, which comprises comparing (i) the concentration of a periostin protein in blood or nasal secretion collected from a test subject with (ii) the concentration of a periostin protein in a normal sample.

[5] The method according to [1] above, which comprises determining that the test subject is suspected of having onset of chronic sinusitis, when (i) the concentration of a periostin protein in blood or nasal secretion collected from a test subject is higher than (ii) the concentration of a periostin protein in a normal sample.

[6] The method according to [4] or [5] above, wherein the normal sample is blood or nasal secretion collected from a patient with allergic rhinitis.

[7] The method according to any one of [1] to [6] above, wherein the measurement is an immunoassay.

[8] An agent for detecting or diagnosing chronic sinusitis, which comprises an antibody that recognizes periostin and which is used to measure the concentration of a periostin protein in blood or nasal secretion and to detect chronic sinusitis.

[9] A kit for detecting or diagnosing chronic sinusitis, which comprises the detection agent according to [8] above and which is used to measure the concentration of a periostin protein in blood or nasal secretion and to detect chronic sinusitis.

[10] A method for analyzing nasal secretion, which comprises measuring the concentration of a periostin protein in the collected nasal secretion.

[11] The method for analyzing nasal secretion according to [10] above, which is characterized in that the concentration of a periostin protein is measured by an immunoassay.

Advantageous Effects of Invention

According to the present invention, the concentration of a periostin protein in a biological sample derived from a test subject, such as blood or chronic sinusitis is diagnosed more simply, more promptly, and with less burden on a patient, so that chronic sinusitis can be detected in the patient based on the obtained analytical value. According to a preferred embodiment of the present invention, it becomes possible to obtain significantly different analytical values between chronic sinusitis patients and allergic rhinitis patients.

BRIEF DESCRIPTION OF DRAWINGS

FIG. 3 is a graph showing the concentration of periostin in serum in the following two chronic sinusitis patient groups: (a) patients with a dysosmia score of 0 (dysosmia (−), 22 cases); and (b) patients with a dysosmia score of 1 (dysosmia (+), 36 cases).

FIG. 4 is a graph showing the concentration of periostin in serum in the following tow chronic sinusitis patient groups: (a) patients with a total of polyp scores from both nasal cavities of 0 to 2 (polyp +, 31 cases); and (b) patients with a total of polyp scores from both nasal cavities of 3 to 4 (polyp ++, 28 cases).

FIG. 5(A) is a graph showing the number of eosinophils in the following two chronic sinusitis patient groups: (a) patients with a serum periostin concentration of less than 95 ng/ml (24 cases); and (b) patients with a serum periostin concentration of 95 ng/ml or more (31 cases).

FIG. 5(B) is a graph showing the relationship between the serum periostin concentration and the number of eosinophils in chronic sinusitis patients (65 cases).

DESCRIPTION OF EMBODIMENTS

Figure 1:
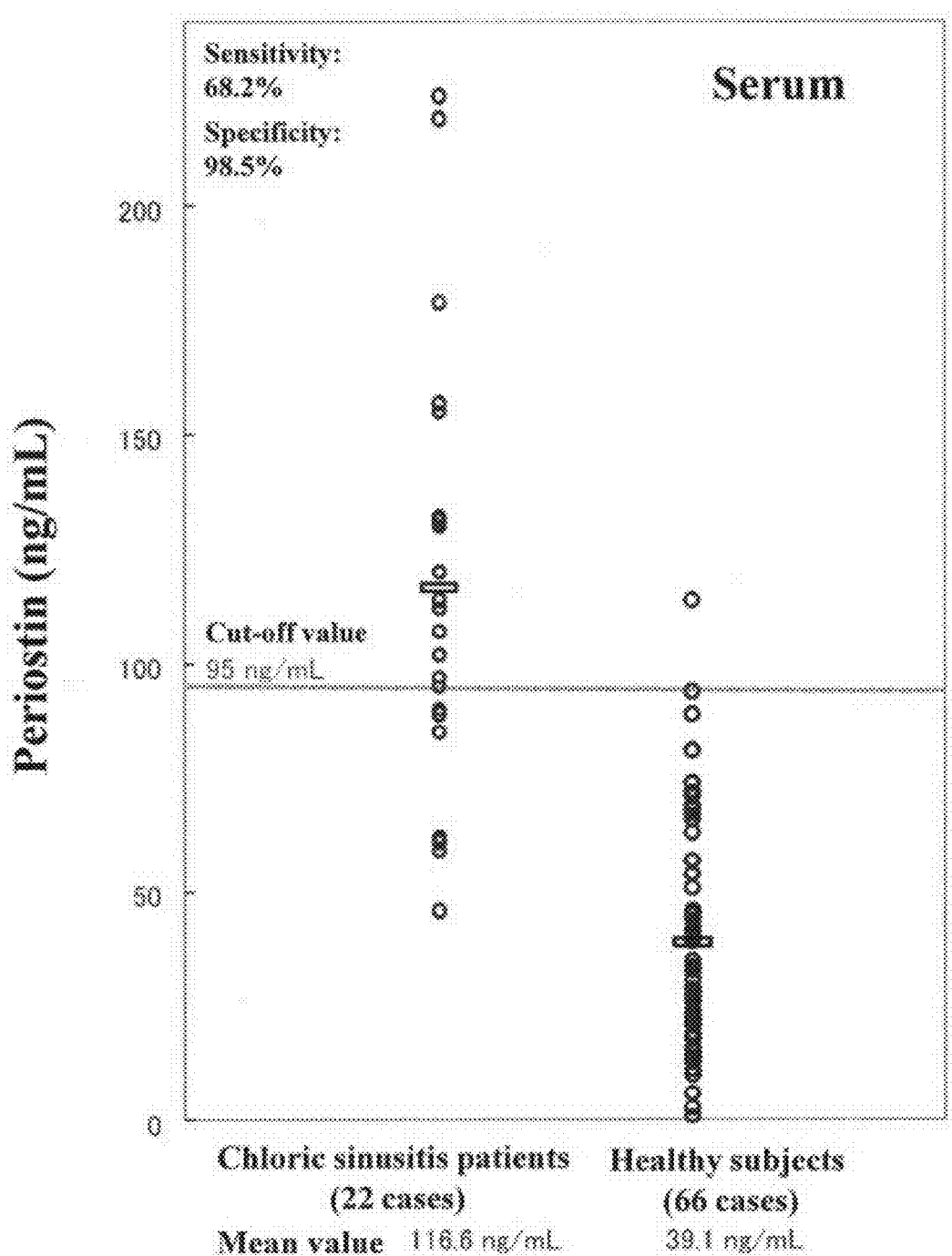
FIG. 1 is a graph showing the results obtained by comparing a chronic sinusitis patient group with a healthy subject group in terms of the analytical value of the concentration of a periostin protein in serum.

Hereinafter, the present invention will be described in detail.

It is to be noted that all publications cited in the present specification, such as prior art publications, and patent literatures such as patent laid-open publications and patent publications, are incorporated herein by reference in their entirety. In additions, the present specification includes all of the contents as disclosed in the claims, specification, and drawings of Japanese Patent Application No. 2011-238913 (filed on Oct. 31, 2011), which is a priority document of the present application.

The present invention relates to an analysis method, which comprises measuring the concentration of a periostin protein in a biological sample derived from a test subject, such as blood or nasal secretion, wherein the method is characterized in that the analysis result is used as an index and is associated with chronic sinusitis.

The present inventors have conducted intensive studies directed towards searching for a method capable of detecting chronic sinusitis more simply, more promptly, and less invasively. As a result, the inventors have found that the concentration of a periostin protein is higher in blood and nasal secretion derived from chronic sinusitis patients, than in blood and nasal secretion derived from healthy subjects or allergic rhinitis patients. Thus, the inventors have found that the analytical value of a periostin protein concentration in the blood or nasal secretion of the chronic sinusitis patients is useful when chronic sinusitis is diagnosed or detected (hereinafter simply referred to as "diagnosed") simply, promptly, and less invasively.

Periostin in the present invention is a protein with a molecular weight of approximately 90 kDa, and it is also referred to as an "osteoblast-specific factor 2" (OSF2; Horiuchi K, Amizuka N, Takeshita S, Takamatsu H, Katsuura M, Ozawa H, Toyama Y, Bonewald L F, Kudo A.; Identification and characterization of a novel protein, periostin, with restricted expression to periosteum and periodontal ligament and increased expression by transforming growth factor beta. J Bone Miner Res. 1999 Jul; 4(7): 1239-49.).

Conventionally, it has been known that allergic disease can be detected using the expression level of a periostin gene as an index (Patent Literature 2 and Non Patent Literature 4). In addition, it has also been known that idiopathic interstitial pneumonia, atopic dermatitis, non-idiopathic interstitial pneumonia such as drug-induced interstitial pneumonia, etc. can be detected using the measurement of the expression level of a periostin gene as an index (Patent Literatures 3 to 5).

Moreover, as described above, the present inventors have reported that the density of periostin in increased even in the tissues in the inflammatory sites of chronic sinusitis or allergic rhinitis (Non Patent Literature 1). Various reports have been conventionally made on such an increase in the density of periostin in inflammatory sites (Non Patent Literatures 5 to 10). However, it has not been previously elucidated that the concentration of a periostin protein is significantly increased in the blood or nasal secretion of a chronic sinusitis patient, and that there is a significant difference between chronic sinusitis patients and allergic rhinitis patients in terms of the concentration of a periostin protein in blood or nasal secretion.

It has been known that periostin has several transcriptional products that can be distinguished from one another based on a difference in the length of the C-terminal side caused by alternative splicing. Herein, the DNA sequence of a transcriptional product of all exons of a human periostin gene is shown in SEQ ID NO: 1 (Accession No. D13666). Moreover, examples of DNA sequences of other splicing variants of human periostin are shown in SEQ ID NOS: 3 and 5 (which have Accession Nos. AY918092 and AY140646, respectively). Furthermore, the amino acid sequences of periostin encoded by the polynucleotides of SEQ ID NOS: 1, 3, and 5 are shown in SEQ ID NOS: 2, 4, and 6, respectively.

In a preferred embodiment of the present invention, periostin comprising the amino acid sequence shown in SEQ ID NO: 2, or periostin comprising a variant derived from the aforementioned amino acid sequence (e.g. periostin consisting of the amino acid sequence shown in SEQ ID NO: 2, 4, or 6), is used as an analytical target.

In the present invention, the analytical value usefully applied to the diagnosis of chronic sinusitis is obtained directly from blood or nasal secretion, among various biological samples derived from test subjects. An analytical value useful for the diagnosis of chronic sinusitis can be obtained by measuring the content of a periostin protein in such a biological sample. When nasal secretion is used as a biological sample, examples of specific objects to be measured include nasal lavage fluid, nasal cavity aspirate, nasal cavity swab, nasopharynx swab, and nasal discharge. Other than these, all types of objects can be used a subjects to be measured in the present invention, as long as they contain a secretion from the mucous membrane around the nasal cavity. On the other hand, when blood is used as a biological sample, examples of specific objects to be measured herein include blood directly collected from the patients, and all types of objects that are obtained by processing blood such that protein components in blood, such as periostin, are not eliminated. Preferred examples of objects to be measured herein include: serum obtained by centrifuging blood after coagulation of the blood; and plasma obtained by centrifuging blood, into which an anticoagulant has been mixed, thereby allowing the removal of blood cells alone.

Nasal secretion can be collected by appropriately applying a known method. For example, nasal secretion can be collected as follows. When nasal secretion is collected in the form of nasal lavage fluid, approximately 10 ml of normal saline is directly injected into the nasal cavity of a patient using a syringe. Even though the syringe is not necessarily inserted into the posterior part of the nasal cavity, injection of normal saline can be sufficiently carried out with water pressure originating from the syringe. The patient is allowed to hold a kidney basin and to tilt his or her face downward, so that the normal sides and the oral cavity into the kidney basin. The normal saline that has flowed downward is recovered with a dropper, and it can be used as a sample for the measurement of the concentration of a periostin protein. Upon injection of normal saline, by allowing a patient to produce a sound, aspiration of the normal saline into the respiratory tract can be prevented, and it also becomes possible to collect the normal saline without infliction of suffering on the patient.

Nasal cavity aspirate can be collected, for example, by inserting a suction trap into the nasal cavity of a patient and then creating a negative pressure in the suction pump.

When nasal secretion is collected in the form of nasal cavity swab or nasopharynx swab, for example, a swab is inserted to a suitable depth along the floor of the nasal cavity, and it is then left at rest for several seconds around the epipharynx or the nasal turbinate. Thereafter, the swab is drawn, while lightly wiping the nasal mucous membrane, so as to collect secretion from the nasal mucous membrane. The swab is then immersed in normal saline to recover nasal secretion from the swab, and the thus recovered nasal secretion can be used as an object to be measured.

For collection of nasal discharge, for example, a collection paper containing nasal discharge, which a patient has used for blowing, is directly immersed in normal saline. Alternatively, a cotton swab portion of a cotton bud is impregnated with nasal discharge on a collection paper, and the cotton swab portion containing the nasal discharge is then immersed in normal saline, so as to recover the nasal secretion. The thus recovered nasal secretion can be used as an object to be measured.

Needless to say, in all cases of using any of the aforementioned methods for collecting nasal secretion, attention should be paid not to dilute the nasal secretion more than necessary, from the viewpoint of analytical precision.

The amount of a periostin protein in blood, nasal secretion, or an object to be measured derived from them, can be specifically measured by an appropriate method. The amount of a periostin protein can be measured, for example, by immunoassay. Examples of such immunoassay include radioimmunoassay (RIA), fluorescence immunoassay (FIA), luminescence immunoassay, and enzyme immunoassay (e.g. Enzyme Immunoassay (EIA) and Enzyme-linked Immunosorbent assay (ELISA)). The immunoassay is preferably ELISA.

Examples of a radioactive substance that can be used for labeling in RIA include $^{125}$I, $^{131}$I, $^{14}$C, $^{3}$H, $^{35}$S, and $^{32}$P.

Examples of a fluorescent substance that can be used for labeling in FIA include fluorescent substances such as Eu (europium), FITC, TMRITC, Cy3, PE, and Texas-Red.

Examples of a luminescent substance that can be used for labeling in luminescence immunoassay include luminol, a luminol derivative, luciferin, and lucigenin.

Examples of enzyme that can be used for labeling in enzyme immunoassay include horseradish peroxidase (HRP), alkaline phosphatase (ALP), and glucose oxidase (GO).

Moreover, a biotin-avidin system can also be used for the binding of an antibody or an antigen with the aforementioned labeling substances.

In all cases of the aforementioned methods, it is preferable that the analytical value of a periostin protein in blood or nasal secretion, namely, the concentration of a periostin protein, be used as an index, and that the analytical value be associated with chronic sinusitis. When the concentration of a periostin protein in blood or nasal secretion is higher than or equal to the predetermined protein concentration, or when the concentration of a periostin protein is high with respect to that of a test subject who has not experienced onset of chronic sinusitis, the aforementioned high concentration may be treated as a strong evidence for demonstrating that the blood or the nasal secretion is derived from a test subject who is suspected of having onset of chronic sinositis.

The "predetermined protein concentration" used as a standard for determining that the blood or the nasal secretion is derived from a test subject who is suspected of having onset of chronic sinusitis can be obtained, for example, as follows. When the amount of a periostin protein in the blood or nasal secretion of a patient who is suspected of having onset of chronic sinusitis is higher than or equal to the "predetermined protein concentration," it can be determined that the blood or the nasal secretion is a biological sample derived from the test subject suspected of having onset of chronic sinusitis.

In order to obtain the above-described "predetermined protein concentration," it is preferable that, first of all, with regard to a plurality of test subjects who are determined to have onset of chronic sinusitis and a plurality of test subjects who are determined not to have onset of chronic sinusitis, who have been diagnosed according to another conventionally known diagnostic method, the concentration of a periostin protein in blood or nasal secretion derived from each test subject be measured, and that the thus measured periostin protein concentrations be then subjected to statistical processing, thereby obtaining the "predetermined protein concentration." In this operation, the necessary number of cases of text subjects who will be subjects to be measure herein is 2 or more for each of the two above types of test subjects, and it is, for example, 5 or more cases, 10 or more cases, 50 or more cases, or 100 or more cases. Using a larger number of cases of test subjects, a more reliable "predetermined protein concentration" can be obtained.

An example of the statistic processing in an analysis using a Receiver-Operating-Characteristics (ROC) curve.

Herein, as a method of obtaining an optimal threshold (cut-off value) used as the "predetermined protein concentration" from the ROC curve, a method using the Youden index (sensitivity+specificity−1) is generally applied (Akobeng, A K, et al., *Acta Paediatrica* 96: 644-647, 2007). In this method, a point at which the Youden index (sensitivity+specificity−1) becomes the maximum indicates a point at which both the sensitivity and the specificity have well-balanced values. Thus, the value showing these diagnostic results is defined as a cut-off value, and it is preferably adopted as the "predetermined protein concentration."

Even in a test subject who is determined not to have onset of chronic sinusitis according to another conventionally known diagnostic method, there is a possibility that the concentration of a periostin protein in the blood or nasal secretion of the test subject may be increased due to other allergic diseases and the like. Accordingly, it is desirable that cases showing a specific periostin protein concentration should be excluded particularly from a group of test subjects who do not have onset of chronic sinusitis in the above-described statistical processing.

With regard to the "predetermined protein concentration" of periostin that can be used as a standard for suspicion of the onset of chronic sinusitis in the present invention, according to the studies conducted by the present inventors, when blood is used as a biological sample, the concentration of periostin in serum is, for example, 50 ng/mL, 55 ng/mL, 60 ng/mL, 65 ng/mL, 70 ng/mL, 75 ng/mL, 80 ng/mL, 81 ng/mL, 82 ng/mL, 83 ng/mL, 84 ng/mL, 85 ng/mL, 86 ng/mL, 87 ng/mL, 88 ng/mL, 89 ng/mL, 90 ng/mL, 91 ng/mL, 92 ng/mL, 93 ng/mL, 94 ng/mL, 95 ng/mL, 96 ng/mL, 97 ng/mL, 98 ng/mL, 99 ng/mL, 100 ng/mL, 101 ng/mL, 102 ng/mL, 103 ng/mL, 104 ng/mL, 105 ng/mL, 106 ng/mL, 107 ng/mL, 108 ng/mL, 109 ng/mL, 110 ng/mL, 115 ng/mL, 120 ng/mL, or 130 ng/mL. It is typically 95 ng/mL. When the concentration of a periostin protein in the serum of a patient to be diagnosed is higher than or equal to the aforementioned "predetermined protein concentration," it can be determined that the patient is suspected of having onset of chronic sinusitis.

Moreover, according to the studies conducted by the present inventors, an upper limit may be established for the value of the "predetermined protein concentration" in serum that can be used as a standard for determining onset of chronic sinusitis, wherein the concentration of a periostin protein in the serum does not exceed the predetermined value only with onset of chronic sinusitis. As specific example, 500 ng/mL, 490 ng/mL, 480 ng/mL, 470 ng/mL, 460 ng/mL, 450 ng/mL, 400 ng/mL, 390 ng/mL, 380 ng/mL, 370 ng/mL, 360 ng/mL, 350 ng/mL, 340 ng/mL, 330 ng/mL, 320 ng/mL, 310 ng/mL, or 300 ng/mL is defined as a standard. When the obtained value exceeds these standard values, it can be determined that the patient is suspected to be affected with pathological conditions other than chronic sinusitis. On the other hand, when the obtained value is smaller than or equal to these standard values and is also greater than or equal to the "predetermined protein concentration," it can be determined that the patient is suspected of having onset of chronic sinusitis.

Furthermore, according to the studies conducted by the present inventors, when nasal secretion is used as a biological sample, the "predetermined protein concentration" of periostin is, for example, 0.5 ng/mL, 0.6 ng/mL, 0.7 ng/mL, 0.8 ng/mL, 0.9 ng/mL, or 1.0 ng/mL, in terms of the concentration of nasal lavage fluid obtained after the nasal cavity has been washed with 10 ml of normal saline. It is typically 0.8 ng/mL. When the measured concentration of a periostin protein in nasal lavage fluid derived from a test subject is higher than or equal to the above-described "predetermined protein concentration," it can be determined that the test subject is suspected of having onset of chronic sinusitis.

Further, according to the studies conducted by the present inventors, up upper limit may be established for the value of the "predetermined protein concentration" in nasal secretion that can be used as a standard for determining onset of chronic sinusitis, wherein the concentration of a periostin protein in the nasal secretion does not exceed the predetermined value only with onset of chronic sinusitis. As specific examples, in terms of the concentration of a periostin protein in nasal lavage fluid obtained when the nasal cavity has been washed with 10 ml of normal saline, 20 ng/mL, 19 ng/mL, 18 ng/mL, 17 ng/mL, 16 ng/mL, 15 ng/mL, 14 ng/mL, 13 ng/mL, 12 ng/mL, 11 ng/mL, or 10 ng/mL is defined as standard. When the obtained value exceeds these standard values, it can be determined that the patient is suspected to be affected with pathological conditions other than chronic sinusitis. On the other hand, when the obtained value is smaller than or equal to these standard values and is also greater than or equal to the "predetermined protein concentration," it can be determined that the patient is suspected of having onset of chronic sinusitis.

It is to be noted that the aforementioned values of the "predetermined protein concentration" in blood and nasal secretion are provided for illustrative purposes only. Needless to say, it is desirable that a suitable "predetermined protein concentration" should be previously determined by individual practitioners according to the above-described method, before implementation of the present invention.

Further, as a method of providing a standard for determining whether a biological sample is derived from a test subject who is suspected of having onset of chronic sinusitis, the following method can be adopted.

Specifically, (i) the concentration of a periostin protein in blood or nasal lavage fluid collected from a test subject is compared with (ii) the concentration of a periostin protein in a normal sample.

The "normal sample" means blood or nasal lavage fluid collected from a test subject who is determined not to have onset of chronic sinusitis. The test subject who is determined not to have onset of chronic sinusitis map be a subject who has onset of a disease (e.g. allergic rhinitis) other than chronic sinusitis, as well as a healthy subject. As the "concentration of a periostin protein in a normal sample," for example, the concentration of a periostin protein in blood or nasal secretion derived from each of a plurality of test subjects who are determined not to have onset of chronic sinusitis, is measured, and thereafter, a mean value of the measured periostin protein concentrations is obtained. Thus, such a mean value of the periostin protein concentrations in the test subjects who do not have onset of chronic sinusitis may be adopted. Upon obtaining a mean value, the necessary number of cases of test subjects who will be subjects to be measured is 2 or more, and it is, for example, 5 or more cases, 10 or more cases, 50 or more cases, or 100 or more cases. Using a larger number of cases of test subjects, a more reliable mean value can be obtained.

When (i) the concentration of a periostin protein in blood or nasal lavage fluid collected from a test subject is higher than (ii) the concentration of a periostin protein in a normal sample, it can be determined that the test subject is suspected of having onset of chronic sinusitis.

In this case, as method of providing a standard for determining that a test subject is suspected of having onset of chronic sinusitis, the following method is more preferable adopted. First, with regard to a plurality of test subjects who are determined to have onset of chronic sinusitis and a plurality of test subjects who are determined not to have onset of chronic sinusitis, who have been determined according to another conventionally known diagnostic method, the concentration of a periostin protein in a biological sample (blood or nasal secretion) derived from each test subject is measured, and a mean value of the thus measured periostin protein concentrations is then obtained. A mean value in the test subjects who have onset of chronic sinusitis is defined as A, a mean value in the test subjects who do not have onset of chronic sinusitis is defined as B, and then, $C=[(A-B)/B] \times 100(\%)$ is calculated. The thus obtained value C is a mean value of the periostin protein concentrations that are increased in biological samples derived from chronic sinusitis patients, determined not to have onset of chronic sinusitis. Using this value as a standard, the presence or absence of the onset of chronic sinusitis can be determined.

That is to say, the concentration of a periostin protein in blood or nasal secretion derived from a patient who is suspected of having onset of chronic sinusitis is measured, and when the measured value is greater than the value D obtained from the formula: $B \times (C/100 \div 1)$, it can be determined that the patient is suspected of having onset of chronic sinusitis.

When aforementioned values A and B are obtained, the necessary number of cases of test subjects who will be subjects to be measured is 2 or more, and it is, for example, 5 or more cases, 10 or more cases, 50 or more cases, or 100 or more cases. Using a larger number of cases of test subjects, more reliable values A and B can be obtained. With an increase in reliability for the values A and B, reliability for the values C and D, which are obtained based on the values A and B, is also increased.

The results of the analytical values according to the present invention are useful, when biological samples derived from test subjects who are suspected of having onset of chronic sinusitis are distinguished from biological samples derived from test subjects who are determined not to have onset of chronic sinusitis (e.g., biological samples derived from allergic rhinitis patients, biological samples derived from healthy subjects, etc.) according to the aboveexemplified determination method, and the analytical value results can be used to simply, promptly, and less invasively detect chronic sinusitis.

The analysis results according to the present invention can be used to assist the definitive diagnosis of chronic sinusitis, for example. When the definitive diagnosis of chronic sinusitis is made, the aforementioned analysis results may be combined with at least one selected from the group consisting of the results of physical findings, imaging test, histological examinations, biochemical test, microbiological tests, and the like, so that the definitive diagnosis of chronic sinusitis may be made in a comprehensive manner.

Moreover, utilizing the phenomenon that the concentration of a periostin protein in the blood or nasal secretion of a chronic sinusitis patient is decreased by the calming of the inflammation and is increased by the aggravation thereof, the analysis method according to the present invention can also be used as a method for grasping the degree of chronic sinusitis in each patient and a change thereof. That is, by continuously applying the analysis method according to the present invention to the biological sample of a patient who has been determined to be suspected of having onset of chronic sinusitis by the analysis method according to the present invention or by another diagnostic method, a change in the degree of chronic sinusitis in the patient is detected, and the progression is then elucidated, so that it can be used as means for knowing the validity of various types of therapeutic methods applied to the aforementioned patient, etc.

Furthermore, the present invention further includes an invention relating to an antibody recognizing periostin that is used as a diagnostic agent for chronic sinusitis. The antibody recognizing periostin used in the present invention may be an antibody well known to a person skilled in the art. For example, a polyclonal antibody or a monoclonal antibody (Milstein C, et al., 1983, Nature 305 (5934): 537-40) may be used. For example, as a polyclonal antibody reacting against periostin, blood may be collected from a mammal sensitized with an antigen (periostin or a partial peptide thereof), and a matter contained in serum separated from the collected blood according to a known method may be directly used. Otherwise, a fraction containing a polyclonal antibody may be further isolated from the aforementioned serum, as necessary, and it may be then used. On the other hand, in order to obtain a monochlonal antibody, immunocytes are removed from the aforementioned mammal sensitized with an antigen, and are then fused with myeloma cells and the like. The obtained hybridomas are subjected to cloning, an antibody is then recovered from the obtained culture, and it can be then used as a monoclonal antibody.

The diagnostic agent for chronic sinusitis according to the present invention, which comprises an antibody recognizing periostin, may be prepared in the form of a diagnostic kit for chronic sinusitis comprising an antibody recognizing periostin, which includes a vessel and a label. It may be described on the vessel or on the label attached to the vessel that the present kit is used for detection or diagnosis of chronic sinusitis. In addition, the present kit may also comprise other items, such as an instruction manual.

The above-described diagnostic agent for chronic sinusitis and diagnostic kit for chronic sinusitis according to the present invention are used to measure the concentration of a periostin protein in blood or nasal secretion, so as to detect chronic sinusitis. For example, the present diagnostic agent and diagnostic kit can be used for the above-described method for detecting or diagnosing chronic sinusitis according to the present invention.

Moreover, needless to say, the above-described diagnostic agent for chronic sinusitis and diagnostic kit for chronic sinusitis according to the present invention can be used for observing the proceedings of the aforementioned chronic sinusitis patients.

Hereinafter, the present invention will be more specifically described in the following examples. However, these examples are not intended to limit the scope of the present invention.

EXAMPLES

Example 1

Serum periostin concentration in the blood collected from test subjects, from whom informed consent had previously been obtained, was analyzed as follows according to an ELISA method using an anti-periostin antibody.

First, 100 µl of SS18A (rat monoclonal anti-periostin antibody) diluted to a concentration of 2 µg/mL with phosphate-buffered saline (PBS) (an aqueous solution (pH 7.4) containing 137 mM sodium chloride, 2.68 mM potassium chloride, 1.47 mM potassium dihydrogen phosphate and 8.04 mM disodium hydrogen phosphate) was poured into each well of a 96-well plate for ELISA, and it was then left at rest at 25° C. for 12 hours or longer, so that SS18A was adsorbed on the bottom of each well. Thereafter, the well was washed with washing solution (PBS containing 0.05% Tween-20) three times, and 250 µl of blocking solution (50 mM Tris buffer (pH 8.0) containing 0.5% casein, 100 mM sodium chloride, and 0.1% sodium azide) was then poured into the resulting well. The well was left at rest at 4° C. for 12 hours or longer. Thereafter, the well was washed with washing solution five times, and 100 µl of serum that had been 201-fold diluted with an analyte dilution solution with the same composition as that of the blocking solution was then poured into the resulting well. The well was left at rest at 25° C. for 12 hours or longer, so that periostin in the serum was captured by SS18A adsorbed on the well. Thereafter, the well was washed with washing solution five times, and 100 µl of SS17B (rat monoclonal anti-periostin antibody) labeled with horseradish peroxidase (HRP), which had been diluted to 50 ng/mL with buffer with the same composition as that of the blocking solution, was then poured into the resulting well. The well was left at rest at 25° C. for 90 minutes, so that the HRP-labeled SS17B was allowed to bind to the periostin captured by SS18A. Thereafter, the well was washed with washing solution five times, and 100 µl of HRP substrate solution (0.8 mM TMBZ, 2.5 mM hydrogen peroxide, 30 mM disodium hydrogen phosphate, and 20 mM citrate buffer) was then poured into the resulting well. The mixture was reacted at 25° C. for 10 minutes, and the reaction was then terminated with 0.7 N sulfuric acid. Subsequently, the absorbance at 450 nm was measured using an absorption spectrometer (Plate Reader/Counter (manufactured by Bio-Rad Laboratories, Inc.)).

The aforementioned SS18A and SS17B were produced as follows. That is, a recombinant periostin protein was injected into the plantar portion of a Wistar rat (Nippon Charles River). Three days later, popliteal, inguinal, and iliac lymph node were removed from the rat, and they were then fused with Sp2/0 myeloma cells. From the grown fused cell lines, two clones were established, and were named as "SS18A" and "SS17B." It is to be noted that a protein prepared according to the method described in Journal of Allergy Clinical Immunology, vol. 118, 98-104, 2006 was used as a recombinant periostin protein.

Moreover, a dilution series of purified periostin proteins that had been expressed in *Escherichia coli* were also measured, and a periostin concentration-absorbance standard curve in the ELISA method was then produced.

The absorbance measured with regard to periostin derived from serum was applied to the produced periostin concentration-absorbance standard curve, and the periostin concentration in serum was then calculated based on the corresponding absorbance.

The results obtained by measuring the periostin concentration in serum according to the above-described method, in both test subjects diagnosed to have chronic sinusitis according to the conventional method and healthy subjects not having chronic sinusitis, are shown in FIG. 1. As shown in FIG. 1, a mean value of the serum periostin concentrations in the chronic sinusitis patients (22 cases) was 116.6 ng/mL. On the other hand, a mean value of the serum periostin concentrations in the healthy subjects (66 cases) was 39.1 ng/mL.

With regard to the thus measured serum periostin concentration, in order to find an optimal threshold (cut-off value) that can be used to extract chronic sinusitis from the population (all cases (88 cases) in which the serum periostin concentration was measured), studies were conducted using a Receiver-Operating-Characteristics (ROC) curve. Specifically, determination of a cut-off value and the measurement of diagnostic accuracy using the determined cut-off value were carried out as follows.

First, a ROC analysis was carried out based on the measurement results of serum periostin concentration. As a result, the area under the ROC curve (area under curve [AUC]) was 0.948 (95% CI, 0.903-0.994), and thus, it was statistically significant ($P<0.001$). Consequently, "95 ng/mL" could be determined as a candidate for the cut-off value.

With regard to a chronic sinusitis patient group (n=22), the upper limit of 95% confidence interval of the mean value was obtained. As a result, the upper limit was found to be 147.9 ng/ml.

When the cut-off value of the concentration of a periostin protein in serum was determined to be 95 ng/ml, the sensitivity was 68.2% and the specificity was 98.5%. From these results, it was found that when the cut-off value is determined to be 95 ng/ml, chronic sinusitis can be detected with relatively high accuracy.

In the present example, it was suggested that chronic sinusitis can be detected with high accuracy by using the above-determined cut-off value as the "predetermined protein concentration."

Example 2

In the present example, nasal lavage fluid collected from test subjects, from whom informed consent had previously been obtained, was used as nasal secretion, and the periostin concentration in the nasal lavage fluid was analyzed.

Collection and preparation of the nasal lavage fluid for the measurement of the periostin concentration were specifically carried out as follows. First, using a syringe, 10 ml of normal saline was directly injected into each patient. even though the syringe was not necessarily inserted into the posterior part of the nasal cavity, injection of normal saline could be sufficiently carried out with water pressure originating from the syringe. The patient was allowed to hold a kidney basin and to tilt his or her face downward, so that the normal saline injected into the nasal cavity could flow through the nasal cavities on both sides and the oral cavity into the kidney basin. The normal saline was recovered from the kidney basin using a dropper, and it was then used as a sample for the measurement of the concentration of a periostin protein. Upon injection of normal saline into the nasal cavity, by allowing a patient to produce a sound, aspiration of the normal saline into the respiratory tract can be prevented, and it also becomes possible to collect the normal saline without infliction of suffering on the patient.

The concentration of periostin in the thus collected nasal lavage fluid was measured as follows according to an ELISA method using an anti-periostin antibody.

First, 100 µl of SS18A (rat monoclonal anti-periostin antibody) diluted to a concentration of 2 µg/mL with phosphate-buffered saline (PBS) (an aqueous solution (pH 7.4) containing 137 mM sodium chloride, 2.68 mM potassium chloride, 1.47 mM potassium dihydrogen phosphate and 8.04 mM disodium hydrogen phosphate) was poured into each well of a 96-well plate for ELISA, and it was then left at rest at 25° C. for 12 hours or longer, so that SS18A was adsorbed on the bottom of each well. Thereafter, the well was washed with washing solution (PBS containing 0.05% Tween-20) three times, and 250 µl of blocking solution (50 mM Tris buffer (pH 8.0) containing 0.5% casein, 100 mM sodium chloride, and 0.1% sodium azide) was then poured into the resulting well. The well was left at reset at 4° C. for 12 hours or longer. Thereafter, the well was washed with washing solution five times, and 100 µl of serum that had been 21-fold diluted with an analyte dilution solution with the same composition as that of the blocking solution was then poured into the resulting well. The well was left at rest at 25° C. for 12 hours or longer, so that periostin in the serum was captured by SS18A adsorbed on the well. Thereafter, the well was washed with washing solution five times, and 100 µl of SS17B (rat monoclonal anti-periostin antibody) labeled with biotin, which had been diluted to 50 ng/mL with buffer with the same composition as that of the blocking solution, was then poured into the resulting well. The well was left at rest at 25° C. for 90 minutes, so that the biotin-labeled SS17B was allowed to bind to the periostin captured by SS18A. The well was washed with washing solution five times. Subsequently, 100 µl of horseradish peroxidase (HRP)-labeled streptavidin, which had been 15,000-fold diluted, was then poured into the resulting well, and was then left at rest at 25° C. for 60 minutes, so that it was allowed to bind to biotin-labeled SS17B. The well was washed with washing solution five times, and 100 µl of HRP substrate solution (0.8 mM TMBZ, 2.5 mM hydrogen peroxide, 30 mM disodium hydrogen phosphate, and 20 mM citrate buffer) was then poured into the resulting well. The mixture was reacted at 25° C. for 20 minutes, and the reaction was then terminated with 0.7 N sulfuric acid. Subsequently, the absorbance at 450 nm was measured using a absorption spectrometer (Plate Reader (manufactured by Bio-Rad Laboratories, Inc.)).

Moreover, a dilution series of purified periostin proteins that had been expressed in *Escherichia coli* were also measured, and a periostin concentration-absorbance standard curve in the ELISA method was then produced.

The absorbance measured with regard to periostin derived from nasal lavage fluid was applied to the produced periostin concentration-absorbance standard curve, and the periostin concentration in nasal lavage fluid was then calculated based on the corresponding absorbance.

Figure 2:
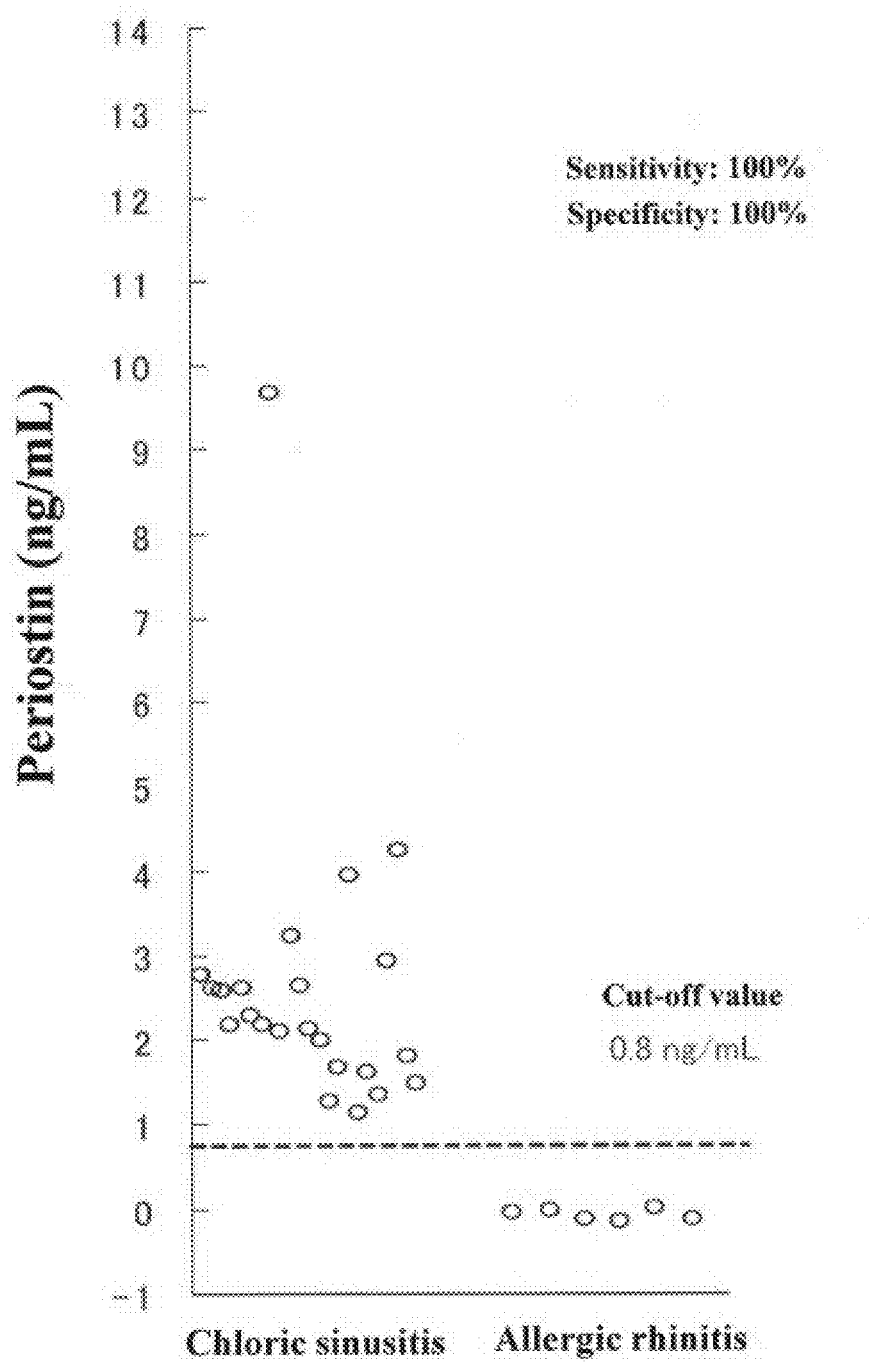
FIG. 2 is a graph showing the results obtained by comparing a chronic sinusitis patient group with an allergic rhinitis patient group in terms of the analytical value of the concentration of a periostin protein in nasal lavage fluid.

The results obtained by measuring the periostin concentration in nasal lavage fluid according to the above-described method, in both test subjects diagnosed to have chronic sinusitis according to the conventional method and allergic rhinitis patients, are shown in FIG. 2. As shown in FIG. 2, a mean value of the nasal lavage fluid periostin concentrations in the chronic sinusitis patients (23 cases) was 2.6 ng/mL. On the other hand, a mean value of the nasal lavage fluid periostin concentrations in the allergic rhinitis patients (6 cases) was 0.1 ng/mL or less.

With regard to the periostin concentration in the nasal lavage fluid measured as above in the present example, in order to find an optimal threshold (cut-off value) that can be used to extract chronic sinusitis from the population (all cases (29 cases) in which the nasal lavage fluid periostin concentration was measure), studies were conducted using a Receiver-Operating-Characteristics (ROC) curve. Specifically, determination of a cut-off value and the measurement of diagnostic accuracy using the determined cut-off value were carried out as follows.

First, a ROC analysis was carried out based on the measurement results of the periostin concentration in the nasal lavage fluid. As a result, the area under the ROC curve (area under curve [AUC]) was 1.000 (95% CI, 1.000-1.000), and thus, it was statistically significant (P<0.001). Consequently, "0.8 ng/mL" could be determined as a candidate for the cut-off value.

With regard to a chronic sinusitis patient group (n=23), the upper limit of 95% confidence interval of the mean value was obtained. As a result, the upper limit was found to be 3.4 ng/ml.

When the cut-off value of the concentration of a periostin protein in the nasal lavage fluid was determined to be 0.8 ng/ml, the sensitivity was 100% and the specificity was 100%. From these results, it was suggested that chronic sinusitis could be distinguished from allergic rhinitis with high accuracy by using the above-determined cut-off value (0.8 ng/mL) as the "predetermined protein concentration." It is to be noted that nasal secretions contained in nasal lavage fluids obtained from individual test subjects in the present example had various different concentrations, and thus that the aforementioned measurement results do not indicate the concentration of a periostin protein contained in the nasal secretion of each test subject. However, as described above, since such a periostin protein is not substantially contained in nasal secretions from allergic rhinitis patients, it is possible to obtain an analytical value capable of distinguishing chronic sinusitis form allergic rhinitis with high accuracy, even by using nasal lavage fluid.

Example 3

In the present example, the relationship between the serum periostin concentration in blood derived from chronic sinusitis patients and the severity of chronic sinusitis was examined.

Examples of an index associated with the severity in the symptoms of chronic sinusitis include the presence or absence of dysosmia, the presence of absence of multiple polyps, the number of eosinophils, the presence or absence of the complication of allergies, and CT (Computed Tomography) scores. In a case in which dysosmia is present, in a case in which multiple adenomatous polyps are presents, in a case in which a large number of eosinophils are present, in a case in which the complication of allergies is present, or in a case in which the CT score is 10 or greater, the symptoms of chronic sinusitis are considered to be more severe.

(1) Relationship Between Serum Periostin Concentration and Dysosmia Score

FIG. 3 shows serum periostin concentrations in the following two patient groups, which ere measured according to the method described in Example 1.

(a) Patients with a dysosmia score of 0 (dysosmia (−), 22 cases)

(b) Patients with a dysosmia score of 1 (dysosmia (+), 36 cases)

The "dysosmia score of 0" is used herein to mean that chronic sinusitis patients do not have dysosmia. The "dysosmia score of 1" is used to mean that chronic sinusitis patients have dysosmia. The presence of dysosmia indicates more sever symptoms. The presence or absence of dysosmia was confirmed by a doctor according to an ordinary method. Just briefly explaining this confirmation method, patients were allowed to smell a plurality of odorous substances having different strength of odors, and thereafter, the level of odor which the patients could recognize was evaluated objectively.

A mean value of serum periostin concentrations in patients with a dysosmia score of 0 was 85.2 ng/ml, and a mean value of serum periostin concentrations in patients with a dysosmia score of 1 was 122.6 ng/ml. The serum periostin concentrations in the patients with a dysosmia score of 1 were significantly higher than those in the patients with a dysosmia score of 0 (P<0.05, t-test).

These results show that there are many patients with sever sinusitis, who are affected with dysosmia, in a high serum periostin concentration group.

(2) Relationship Between Serum Periostin Concentration and Polyp Score

FIG. 4 shows serum periostin concentrations in the following two patient groups, which were measured according to the method described in Example 1.

(a) Patients with a total of polyp scores from both nasal cavities that is 0 to 2 (polyp +, 31 cases)

(b) Patients with a total of polyp scores from both nasal cavities that is 3 to 4 (polyp ++, 28 cases)

The "polyp score of 0" is used herein to mean that there are no polyps in the one nasal cavity of a chronic sinusitis patient; the "polyp score of 1" is used to mean that there is a single polyp in one nasal cavity of a chronic sinusitis patient; and the "polyp score of 2" is used to mean that there are multiple adenomatous polyps in one nasal cavity of a chronic sinusitis patient. The presence of multiple adenomatous polyps indicates that the symptoms are more sever. The presence of absence of a single polyp or multiple adenomatous polyps was confirmed by a doctor according to an ordinary method. Just briefly explaining this confirmation method, the doctor observed the inside of the nose of a patient with a nasopharyngolaryngoscope, and examined the number of polyps and the sites thereof.

A mean value of serum periostin concentrations in patients with a total of polyp scores from both nasal cavities that is 0 to 2, namely, patients with polyp +, was 91.6 ng/ml, and a mean value of serum periostin concentrations in patients with a total of polyp scores from both nasal cavities that is 3 to 4, namely, patients with polyp ++, was 127.0 ng/ml. The serum periostin concentrations in the patients with polyp ++ were significantly higher than those in the patients with polyp + (P<0.5, t-test).

These results show that, when a patient has a high blood periostin concentration, it is highly likely that he or she would be affected with severe chloric sinusitis having multiple adenomatous polyps.

(3) Relationship Between Serum Periostin Concentration and the Number of Eosinophils FIG. 5(A) shows the number of eosinophils in the following two patient groups.

(a) Patients with a serum periostin concentration of less than 95 ng/ml (24 cases)

(b) Patents with a serum periostin concentration of 95 ng/ml or more (31 cases)

The serum periostin concentration was measured according to the method described in Example 1.

The number of eosinophils was measured according to an ordinary method (Hideo EBARA, Medicine 31 (11): 288-290, 1944). Just briefly explaining this confirmation method, the number of eosinophils in the blood of each patient was counted utilizing the phenomenon that such eosinophils have eosinophil granules.

A mean value of the eosinophil numbers in patients with a serum periostin concentration of 95 ng/ml or more was 6.2%, and a mean value of the eosinophil numbers in patients with a serum periostin concentration of less than 95 ng/ml was 3.9%. The number of eosinophils in the patients with a scrum periostin concentration of 95 ng/ml or more was significantly higher than that in the patients with a serum periostin concentration of less than 95 ng/ml ($P<0.05$, ×2 test).

Figure 5B:
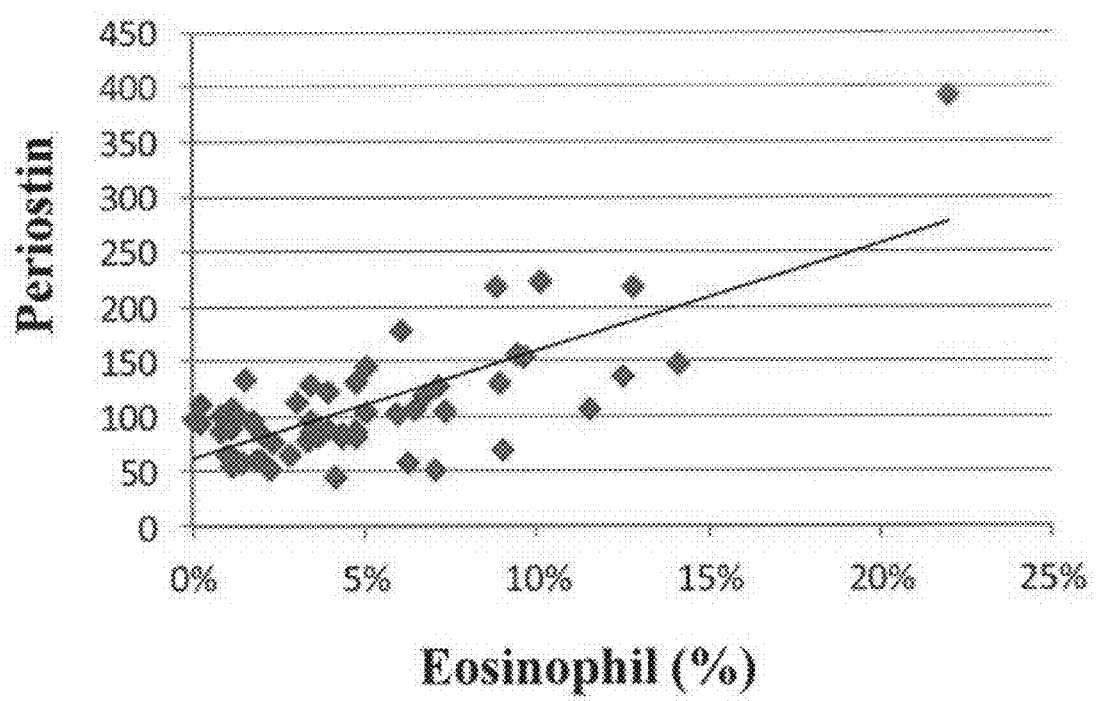
[FIG. 5(B)]

FIG. 5(B) shows the relationship between the serum periostin concentration and the number of eosinophils in chronic sinusitis patients (55 cases). From FIG. 5(B), it is found that the number of eosinophils increases, as the number of periostin in serum increases.

These results show that, when a patient has a high blood periostin concentration, it is highly likely that he or she would have a large number of eosinophils and would be affected with more severe chloric sinusitis.

(4) Relationship Between Serum Periostin Concentration and Allergy Score

Figure 6A:
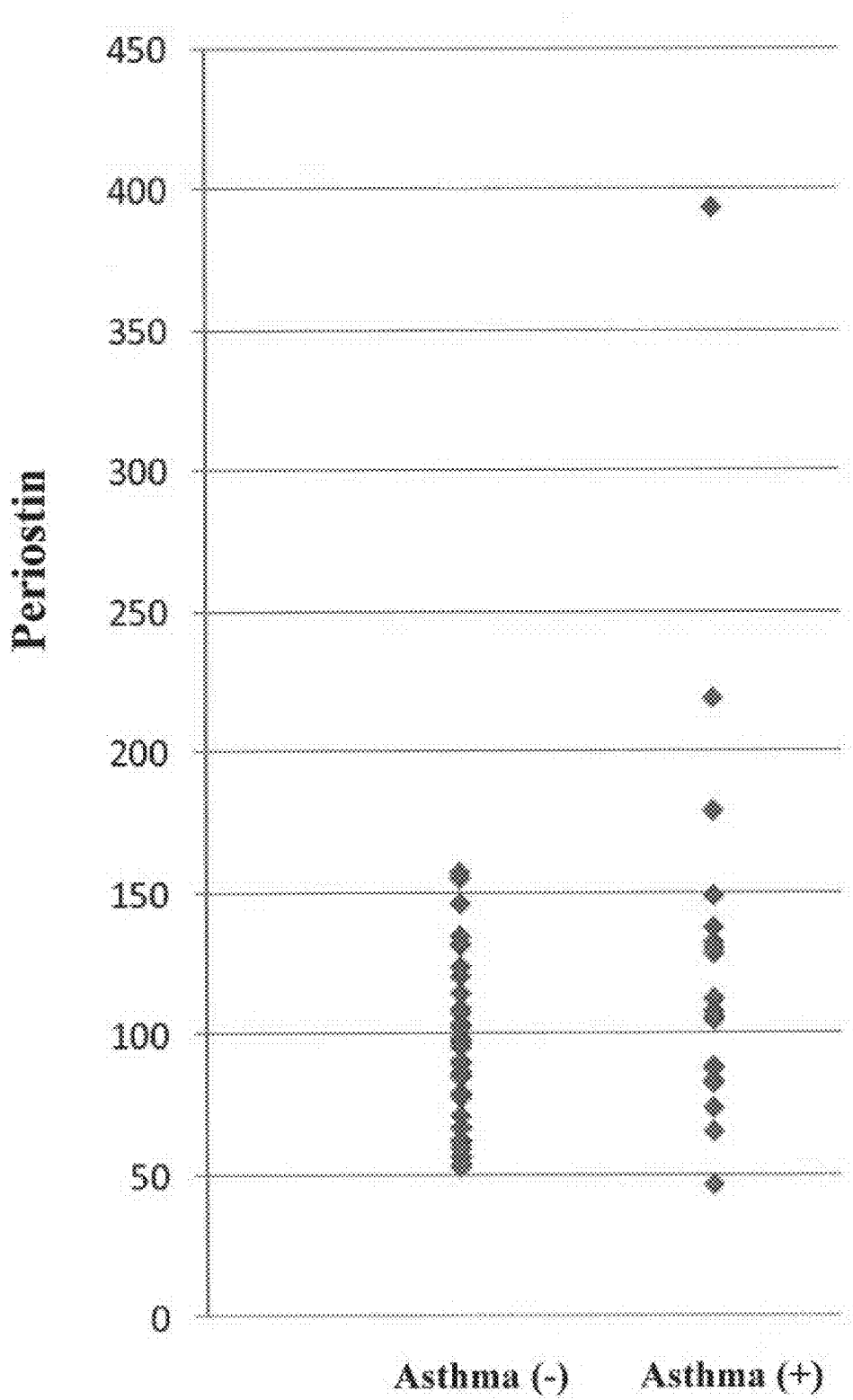
FIG. 6(A) is a graph showing the serum periostin concentration in the following two chronic sinusitis patient groups: (a) patients with an allergy score of 0 to 1 (asthma (−), 38 cases); and, (b) patients with an allergy score of 2 to 3 (asthma (+), 20 cases).

FIG. 6(A) shows the serum periostin concentrations in the following two patients groups, which were measured according to the method described in Example 1.

(a) Patients with an allergy score of 0 to 1 (asthma (−), 38 cases)

(b) Patients with an allergy score of 2 to 3 (asthma (+), 20 cases)

Figure 6B:
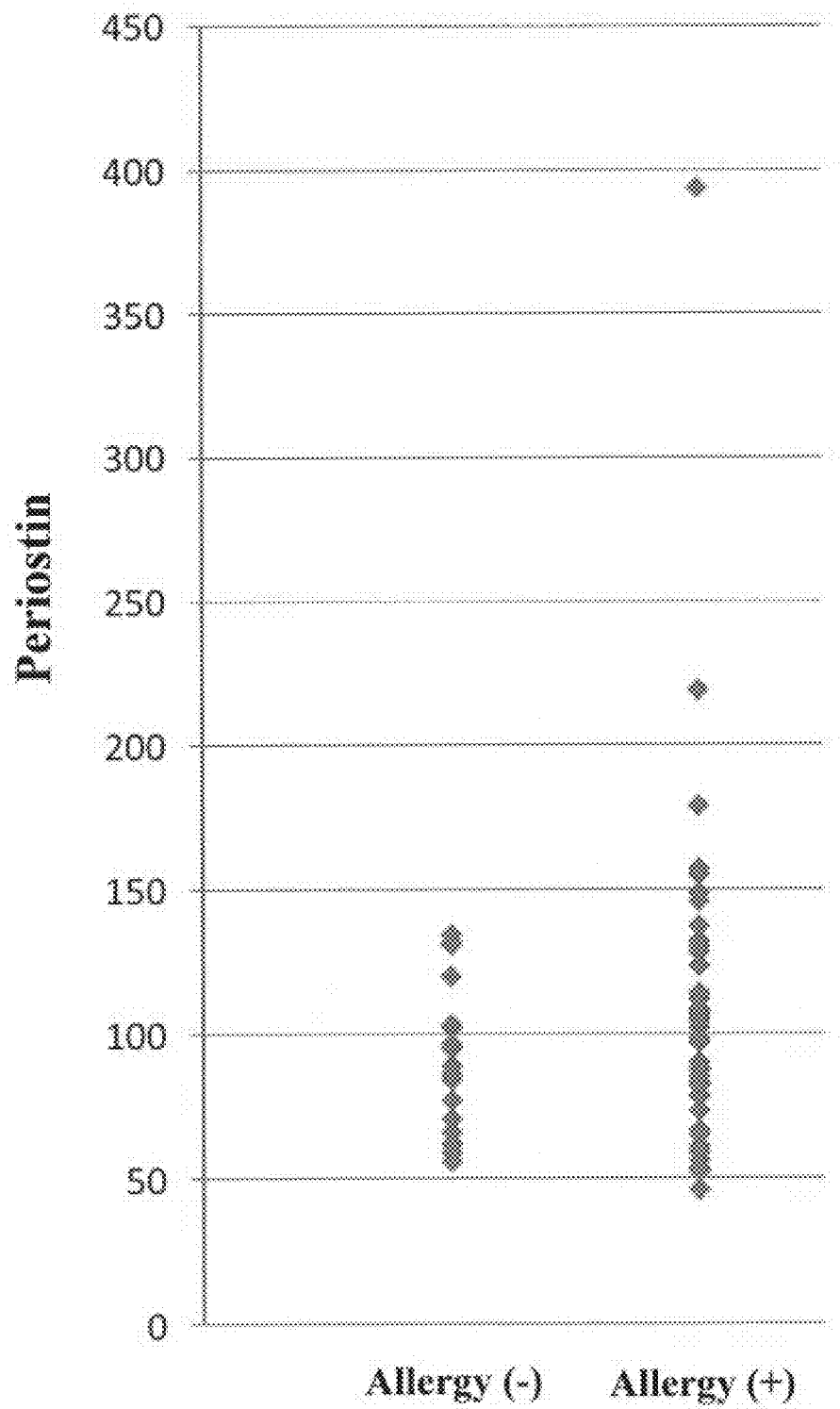
FIG. 6(B) is a graph showing the serum periostin concentration in the following two chronic sinusitis patient groups: (c) patients with an allergy score of 0 (allergy (−), 18 cases); and (d) patients with an allergy score of 1 to 3 (allergy (+), 40 cases).

FIG. 6(B) shows the serum periostin concentrations in the following two patients groups, which were measured according to the method described in Example 1.

(c) Patients with an allergy score of 0 (allergy (−), 18 cases)

(d) Patients with an allergy score of 1 to 3 (allergy (+), 40 cases)

The "allergy score of 0" is used herein to mean that a chronic sinusitis patient does not have either the complication of allergic rhinitis or the complication of asthma; the "allergy score of 1" is used herein to mean that a chronic sinusitis patient has the complication of allergic rhinitis but does not have the complication of asthma; the "allergy score 2" is used herein to mean that a chronic sinusitis patient has the complication of asthma but does not have the complication of allergic rhinitis; and the "allergy score 3" is used herein to mean that a chronic sinusitis patient has both the complication of allergic rhinitis and the complication of asthma. The presence or absence of the complication of asthma and the presence or absence of the complication of allergic rhinitis were confirmed by a doctor according to an ordinary method.

A mean value of serum periostin concentrations in patients with an allergy score of 0 to 1, namely, patients with asthma (−), was 92.4 ng/ml, and a mean value of serum periostin concentrations in patients with an allergy score of 2 to 3, namely, patients with asthma (+), was 125.2 ng/ml. There was no significant difference between the serum periostin concentrations in the patients with asthma (+) and those in the patients with asthma (−) (t-test).

A mean value of serum periostin concentrations in patients with an allergy score of 0, namely, patients with allergy (−), was 90.0 ng/ml, and a mean value of serum periostin concentrations in patients with an allergy score of 1 to 3, namely, patients with allergy (+), was 109.8 ng/ml. There was no significant difference between the serum periostin concentrations in the patients with allergy (+)and those in the patients with allergy (−) (t-test).

From the above results, there was found no significant difference in terms of blood periostin concentration, depending on the presence or absence of the complication of asthma and the presence or absence of allergic disease.

Figure 7:
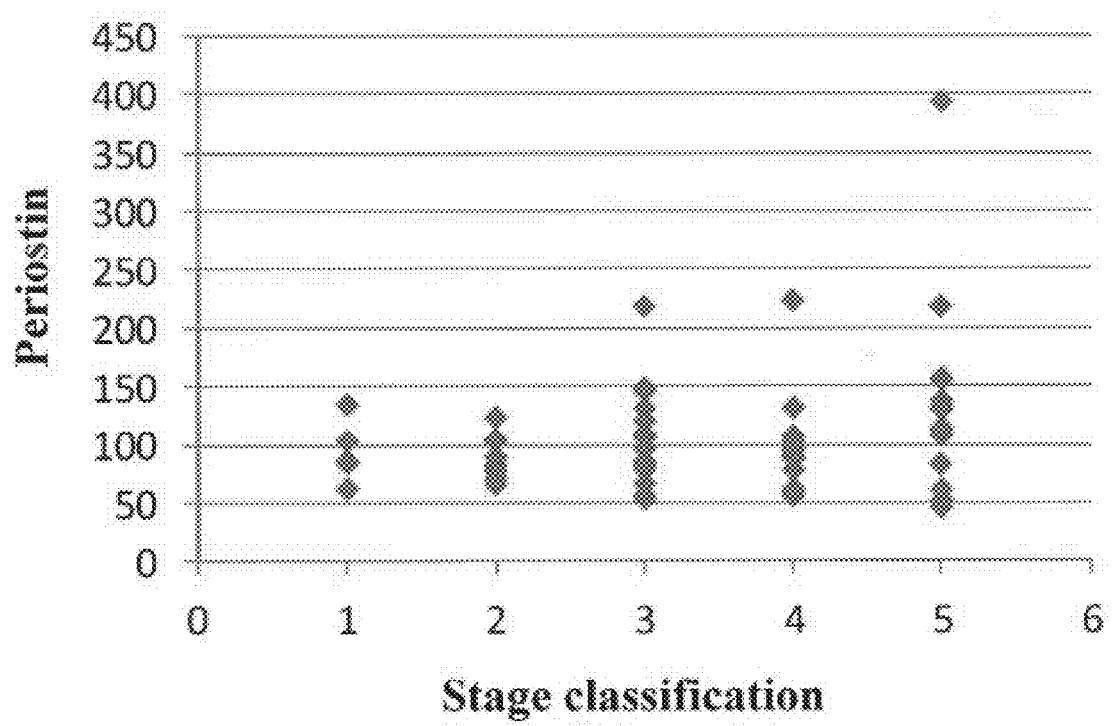
FIG. 7 is a graph showing the serum periostin concentration in the following five chronic sinusitis patient groups: (a) patients with Stage 1 (5 cases); (b) patients with Stage 2 (8 cases); (c) patients with Stage 3 (12 cases); (d) patients with Stage 4 (16 cases); and (e) patients with Stage 5 (15 cases).

(5) Relationship Between Periostin Protein Concentration in Serum and Stage Classification FIG. 7 shows the serum periostin concentrations in the following five patients groups, which were measured according to the method described in Example 1.

(a) Patients with Stage 1 (5 cases)

(b) Patients with Stage 2 (8 cases)

(c) Patients with Stage 3 (12 cases)

(d) Patients with Stage 4 (16 cases)

(e) Patients with Stage 5 (15 cases)

Each of the aforementioned Stages was obtained by dividing chronic sinusitis patients based on imaging findings, the presence or absence of the complication of allergy, and intranasal findings. Stage 1 indicates the mildest symptoms, and Stage 5 indicates the most severe symptoms.

The imaging findings were obtained as follows. The degree of shadow found in the soft tissues in each site of the maxillary antrum, the ethmoid antrum, the frontal sinus, the sphenoid sinus, the olfactory cleavage, and the OMC was classified into the following three stages: "none" (0 point), "low" (1 point), and "high" (2 points). Thus, the shadow degree was graded on a scale of 0 to 12 points for either the left or right nasal cavity, and on a total 24 point-scale.

The presence or absence of the complication of allergy was confirmed by the method described in (4) above, and it was then graded. The intranasal findings were confirmed by the method described in (2) above. Then, as described in (2) above, when there were no polyps, it was defined as 0 point, when there was a single polyp, it was defined as 1 point, and when there were multiple adenomatous polyps, it was defined as 2 points.

Thereafter, based on a total score of the score from the imaging findings, the score from the presence or absence of allergy, and the score from the intranasal findings, the patients were divided into the following groups.

"Stage 1" has a total score of 0 to 4. It means very mild chronic sinusitis.

"Stage 2" has a total score of 5 to 6. It means mild chronic sinusitis.

"Stage 3" has a total score of 7 to 9. It means middle level of chronic sinusitis.

"Stage 4" has a total score of 10 to 14. It means severe chronic sinusitis.

"Stage 5" has a total score of 14 or more. It means the most severe chronic sinusitis.

Mean values of serum periostin concentrations in patients with Stages 1 to 5 were 93.8 ng/ml, 89.3 ng/ml, 103.5 ng/ml, 100 ng/ml, and 132.5 ng/ml, respectively. There was no significant difference in the serum periostin concentrations among the patients with Stages 1 to 5 (×2 test).

From the above results, in terms of blood periostin concentration, there was found no significant difference among the individual stages.

The above results were comprehensively analyzed. As a result, it was found that the more severe the symptoms, the higher the serum periostin concentration that could be obtained in the blood of chronic sinusitis patients.

As described in the above examples, it was found that the concentration of a periostin protein is increased in blood and nasal secretion derived from a chronic sinusitis patient. Thus, by analyzing the concentration of a periostin protein in blood and nasal secretion derived from test subjects, the obtained result can be used as useful information for diagnosing chronic sinusitis. In particular, since the periostin concentration in the blood and nasal secretion from chronic sinusitis patients is higher than that from allergic rhinitis patients, the analytical value of the periostin protein in the blood and nasal secretion was found to be useful, when chronic sinusitis is detected by separating it from allergic rhinitis.

The invention claimed is:

1. A method for detecting and treating chronic sinusitis in a test subject having at least one symptom indicative of chronic sinusitis or allergic rhinitis selected from the group consisting of nasal discharge, nasal obstruction, and post nasal drip, which comprises:
    measuring the concentration of periostin protein in serum collected from the subject;
    detecting onset of chronic sinusitis when the concentration of the periostin protein measured in the serum is 95 ng/mL or more; and
    administering an antibiotic and/or surgical treatment for chronic sinusitis to the test subject with detected onset of chronic sinusitis to treat chronic sinusitis.

2. A method for detecting and treating chronic sinusitis in a test subject having at least one symptom indicative of chronic sinusitis or allergic rhinitis selected from the group consisting of nasal discharge, nasal obstruction, and post nasal drip, which comprises:

measuring the concentration of periostin protein in nasal lavage fluid collected from the subject;

detecting onset of chronic sinusitis when the concentration of the periostin protein measured in the nasal lavage is 0.8 ng/mL or more; and administering an antibiotic and/or surgical treatment for chronic sinusitis to the test subject with detected onset of chronic sinusitis to treat chronic sinusitis.

3. A method for detecting and treating chronic sinusitis in a test subject having at least one symptom indicative chronic sinusitis or allergic rhinitis selected from the group consisting of nasal discharge, nasal obstruction, and postnasal drip, which comprises:

measuring the concentration of periostin protein in blood or nasal secretion collected from the test subject;

determining that the test subject has onset of chronic sinusitis when the concentration of the periostin protein in blood or nasal secretion collected from the test subject is higher than the concentration of the periostin protein in a normal sample; and administering an antibiotic and/or surgical treatment for chronic sinusitis to the test subject determined as having onset of chronic sinusitis to treat chronic sinusitis.

4. The method of claim 1, wherein measuring the concentration is performed by an immunoassay.

5. The method of claim 1, wherein the antibiotic is administered to the test subject.

6. The method of claim 2, wherein the antibiotic is administered to the test subject.

7. The method of claim 3, wherein the antibiotic is administered to the test subject.

8. The method of claim 1, wherein surgical treatment is administered to the test subject.

9. The method of claim 2, wherein surgical treatment is administered to the test subject.

10. The method of claim 3, wherein surgical treatment is administered to the test subject.

\* \* \* \* \*

SEQUENCE LISTING

```
<160> NUMBER OF SEQ ID NOS: 6

<210> SEQ ID NO 1
<211> LENGTH: 3213
<212> TYPE: DNA
<213> ORGANISM: Homo sapiens
<220> FEATURE:
<221> NAME/KEY: CDS
<222> LOCATION: (12)..(2522)

<400> SEQUENCE: 1
agagactcaa g atg att ccc ttt tta ccc atg ttt tct cta cta ttg ctg     50
            Met Ile Pro Phe Leu Pro Met Phe Ser Leu Leu Leu Leu
            1               5                   10 ctt att gtt aac cct ata aac gcc aac aat cat tat gac aag atc ttg     98
Leu Ile Val Asn Pro Ile Asn Ala Asn Asn His Tyr Asp Lys Ile Leu
    15                  20                  25 gct cat agt cgt atc agg ggt cgg gac caa ggc cca aat gtc tgt gcc    146
Ala His Ser Arg Ile Arg Gly Arg Asp Gln Gly Pro Asn Val Cys Ala
30                  35                  40                  45 ctt caa cag att ttg ggc acc aaa aag aaa tac ttc agc act tgt aag    194
Leu Gln Gln Ile Leu Gly Thr Lys Lys Lys Tyr Phe Ser Thr Cys Lys
                50                  55                  60 aac tgg tat aaa aag tcc atc tgt gga cag aaa acg act gtt tta tat    242
Asn Trp Tyr Lys Lys Ser Ile Cys Gly Gln Lys Thr Thr Val Leu Tyr
            65                  70                  75 gaa tgt tgc cct ggt tat atg aga atg gaa gga atg aaa ggc tgc cca    290
Glu Cys Cys Pro Gly Tyr Met Arg Met Glu Gly Met Lys Gly Cys Pro
        80                  85                  90 gca gtt ttg ccc att gac cat gtt tat ggc act ctg ggc atc gtg gga    338
Ala Val Leu Pro Ile Asp His Val Tyr Gly Thr Leu Gly Ile Val Gly
    95                  100                 105 gcc acc aca acg cag cgc tat tct gac gcc tca aaa ctg agg gag gag    386
Ala Thr Thr Thr Gln Arg Tyr Ser Asp Ala Ser Lys Leu Arg Glu Glu
110                 115                 120                 125 atc gag gga aag gga tcc ttc act tac ttt gca ccg agt aat gag gct    434
Ile Glu Gly Lys Gly Ser Phe Thr Tyr Phe Ala Pro Ser Asn Glu Ala
                130                 135                 140 tgg gac aac ttg gat tct gat atc cgt aga ggt ttg gag agc aac gtg    482
Trp Asp Asn Leu Asp Ser Asp Ile Arg Arg Gly Leu Glu Ser Asn Val
            145                 150                 155 aat gtt gaa tta ctg aat gct tta cat agt cac atg att aat aag aga    530
Asn Val Glu Leu Leu Asn Ala Leu His Ser His Met Ile Asn Lys Arg
        160                 165                 170 atg ttg acc aag gac tta aaa aat ggc atg att att cct tca atg tat    578
Met Leu Thr Lys Asp Leu Lys Asn Gly Met Ile Ile Pro Ser Met Tyr
    175                 180                 185 aac aat ttg ggg ctt ttc att aac cat tat cct aat ggg gtt gtc act    626
Asn Asn Leu Gly Leu Phe Ile Asn His Tyr Pro Asn Gly Val Val Thr
190                 195                 200                 205
```

| | | |
|---|---|---|
| gtt aat tgt gct cga atc atc cat ggg aac cag att gca aca aat ggt<br>Val Asn Cys Ala Arg Ile Ile His Gly Asn Gln Ile Ala Thr Asn Gly<br>210 215 220 | 674 | |
| gtt gtc cat gtc att gac cgt gtg ctt aca caa att ggt acc tca att<br>Val Val His Val Ile Asp Arg Val Leu Thr Gln Ile Gly Thr Ser Ile<br>225 230 235 | 722 | |
| caa gac ttc att gaa gca gaa gat gac ctt tca tct ttt aga gca gct<br>Gln Asp Phe Ile Glu Ala Glu Asp Asp Leu Ser Ser Phe Arg Ala Ala<br>240 245 250 | 770 | |
| gcc atc aca tcg gac ata ttg gag gcc ctt gga aga gac ggt cac ttc<br>Ala Ile Thr Ser Asp Ile Leu Glu Ala Leu Gly Arg Asp Gly His Phe<br>255 260 265 | 818 | |
| aca ctc ttt gct ccc acc aat gag gct ttt gag aaa ctt cca cga ggt<br>Thr Leu Phe Ala Pro Thr Asn Glu Ala Phe Glu Lys Leu Pro Arg Gly<br>270 275 280 285 | 866 | |
| gtc cta gaa agg ttc atg gga gac aaa gtg gct tcc gaa gct ctt atg<br>Val Leu Glu Arg Phe Met Gly Asp Lys Val Ala Ser Glu Ala Leu Met<br>290 295 300 | 914 | |
| aag tac cac atc tta aat act ctc cag tgt tct gag tct att atg gga<br>Lys Tyr His Ile Leu Asn Thr Leu Gln Cys Ser Glu Ser Ile Met Gly<br>305 310 315 | 962 | |
| gga gca gtc ttt gag acg ctg gaa gga aat aca att gag ata gga tgt<br>Gly Ala Val Phe Glu Thr Leu Glu Gly Asn Thr Ile Glu Ile Gly Cys<br>320 325 330 | 1010 | |
| gac ggt gac agt ata aca gta aat gga atc aaa atg gtg aac aaa aag<br>Asp Gly Asp Ser Ile Thr Val Asn Gly Ile Lys Met Val Asn Lys Lys<br>335 340 345 | 1058 | |
| gat att gtg aca aat aat ggt gtg atc cat ttg att gat cag gtc cta<br>Asp Ile Val Thr Asn Asn Gly Val Ile His Leu Ile Asp Gln Val Leu<br>350 355 360 365 | 1106 | |
| att cct gat tct gcc aaa caa gtt att gag ctg gct gga aaa cag caa<br>Ile Pro Asp Ser Ala Lys Gln Val Ile Glu Leu Ala Gly Lys Gln Gln<br>370 375 380 | 1154 | |
| acc acc ttc acg gat ctt gtg gcc caa tta ggc ttg gca tct gct ctg<br>Thr Thr Phe Thr Asp Leu Val Ala Gln Leu Gly Leu Ala Ser Ala Leu<br>385 390 395 | 1202 | |
| agg cca gat gga gaa tac act ttg ctg gca cct gtg aat aat gca ttt<br>Arg Pro Asp Gly Glu Tyr Thr Leu Leu Ala Pro Val Asn Asn Ala Phe<br>400 405 410 | 1250 | |
| tct gat gat act ctc agc atg gtt cag cgc ctc ctt aaa tta att ctg<br>Ser Asp Asp Thr Leu Ser Met Val Gln Arg Leu Leu Lys Leu Ile Leu<br>415 420 425 | 1298 | |
| cag aat cac ata ttg aaa gta aaa gtt ggc ctt aat gag ctt tac aac<br>Gln Asn His Ile Leu Lys Val Lys Val Gly Leu Asn Glu Leu Tyr Asn<br>430 435 440 445 | 1346 | |
| ggg caa ata ctg gaa acc atc gga ggc aaa cag ctc aga gtc ttc gta<br>Gly Gln Ile Leu Glu Thr Ile Gly Gly Lys Gln Leu Arg Val Phe Val<br>450 455 460 | 1394 | |
| tat cgt aca gct gtc tgc att gaa aat tca tgc atg gag aaa ggg agt<br>Tyr Arg Thr Ala Val Cys Ile Glu Asn Ser Cys Met Glu Lys Gly Ser<br>465 470 475 | 1442 | |
| aag caa ggg aga aac ggt gcg att cac ata ttc cgc gag atc atc aag<br>Lys Gln Gly Arg Asn Gly Ala Ile His Ile Phe Arg Glu Ile Ile Lys<br>480 485 490 | 1490 | |
| cca gca gag aaa tcc ctc cat gaa aag tta aaa caa gat aag cgc ttt<br>Pro Ala Glu Lys Ser Leu His Glu Lys Leu Lys Gln Asp Lys Arg Phe<br>495 500 505 | 1538 | |
| agc acc ttc ctc agc cta ctt gaa gct gca gac ttg aaa gag ctc ctg<br>Ser Thr Phe Leu Ser Leu Leu Glu Ala Ala Asp Leu Lys Glu Leu Leu | 1586 | |

```
                                        -continued 510              515              520              525
aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530              535              540 aag gga atg act agt gaa gaa aaa gaa att ctg ata cgg gac aaa aat     1682
Lys Gly Met Thr Ser Glu Glu Lys Glu Ile Leu Ile Arg Asp Lys Asn
                545              550              555 gct ctt caa aac atc att ctt tat cac ctg aca cca gga gtt ttc att     1730
Ala Leu Gln Asn Ile Ile Leu Tyr His Leu Thr Pro Gly Val Phe Ile
                560              565              570 gga aaa gga ttt gaa cct ggt gtt act aac att tta aag acc aca caa     1778
Gly Lys Gly Phe Glu Pro Gly Val Thr Asn Ile Leu Lys Thr Thr Gln
                575              580              585 gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590              595              600              605 gaa ttg aaa tca aaa gaa tct gac atc atg aca aca aat ggt gta att     1874
Glu Leu Lys Ser Lys Glu Ser Asp Ile Met Thr Thr Asn Gly Val Ile
                610              615              620 cat gtt gta gat aaa ctc ctc tat cca gca gac aca cct gtt gga aat     1922
His Val Val Asp Lys Leu Leu Tyr Pro Ala Asp Thr Pro Val Gly Asn
                625              630              635 gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
                640              645              650 aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
                655              660              665 aca act aaa att ata acc aaa gtt gtg gaa cca aaa att aaa gtg att     2066
Thr Thr Lys Ile Ile Thr Lys Val Val Glu Pro Lys Ile Lys Val Ile
670              675              680              685 gaa ggc agt ctt cag cct att atc aaa act gaa gga ccc aca cta aca     2114
Glu Gly Ser Leu Gln Pro Ile Ile Lys Thr Glu Gly Pro Thr Leu Thr
                690              695              700 aaa gtc aaa att gaa ggt gaa cct gaa ttc aga ctg att aaa gaa ggt     2162
Lys Val Lys Ile Glu Gly Glu Pro Glu Phe Arg Leu Ile Lys Glu Gly
                705              710              715 gaa aca ata act gaa gtg atc cat gga gag cca att att aaa aaa tac     2210
Glu Thr Ile Thr Glu Val Ile His Gly Glu Pro Ile Ile Lys Lys Tyr
                720              725              730 acc aaa atc att gat gga gtg cct gtg gaa ata act gaa aaa gag aca     2258
Thr Lys Ile Ile Asp Gly Val Pro Val Glu Ile Thr Glu Lys Glu Thr
                735              740              745 cga gaa gaa cga atc att aca ggt cct gaa ata aaa tac act agg att     2306
Arg Glu Glu Arg Ile Ile Thr Gly Pro Glu Ile Lys Tyr Thr Arg Ile
750              755              760              765 tct act gga ggt gga gaa aca gaa gaa act ctg aag aaa ttg tta caa     2354
Ser Thr Gly Gly Gly Glu Thr Glu Glu Thr Leu Lys Lys Leu Leu Gln
                770              775              780 gaa gag gtc acc aag gtc acc aaa ttc att gaa ggt ggt gat ggt cat     2402
Glu Glu Val Thr Lys Val Thr Lys Phe Ile Glu Gly Gly Asp Gly His
                785              790              795 tta ttt gaa gat gaa gaa att aaa aga ctg ctt cag gga gac aca ccc     2450
Leu Phe Glu Asp Glu Glu Ile Lys Arg Leu Leu Gln Gly Asp Thr Pro
                800              805              810 gtg agg aag ttg caa gcc aac aaa aaa gtt caa ggt tct aga aga cga     2498
Val Arg Lys Leu Gln Ala Asn Lys Lys Val Gln Gly Ser Arg Arg Arg
                815              820              825 tta agg gaa ggt cgt tct cag tga aaatccaaaa accagaaaaa aatgtttata   2552
```

```
Leu Arg Glu Gly Arg Ser Gln
        830                 835 caaccctaag tcaataacct gaccttagaa aattgtgaga gccaagttga cttcaggaac    2612
tgaaacatca gcacaaagaa gcaatcatca ataattctg aacacaaatt taatatttt     2672 ttttctgaat gagaaacatg agggaaattg tggagttagc ctcctgtggt aaaggaattg   2732
aagaaaatat aacaccttac acccttttc atcttgacat taaaagttct ggctaacttt    2792
ggaatccatt agagaaaaat ccttgtcacc agattcatta caattcaaat cgaagagttg   2852
tgaactgtta tcccattgaa aagaccgagc cttgtatgta tgttatggat acataaaatg   2912
cacgcaagcc attatctctc catgggaagc taagttataa aaataggtgc ttggtgtaca   2972
aaacttttta tatcaaaagg ctttgcacat ttctatatga gtgggtttac tggtaaatta   3032
tgttattttt tacaactaat tttgtactct cagaatgttt gtcatatgct tcttgcaatg   3092
catatttttt aatctcaaac gtttcaataa aaccattttt cagatataaa gagaattact   3152
tcaaattgag taattcagaa aaactcaaga tttaagttaa aaagtggttt ggacttggga   3212
a                                                                   3213

<210> SEQ ID NO 2
<211> LENGTH: 836
<212> TYPE: PRT
<213> ORGANISM: Homo sapiens

<400> SEQUENCE: 2

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240
```

```
Ile Glu Ala Glu Asp Leu Ser Ser Phe Arg Ala Ala Ile Thr
            245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
            275                 280                 285

Arg Phe Met Gly Asp Lys Val Ala Ser Glu Ala Leu Met Lys Tyr His
            290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
            325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
            370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
            405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
            450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
            565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655
```

```
Arg Gly Ser Thr Phe Lys Glu Ile Pro Val Thr Val Tyr Thr Thr Lys
            660                 665                 670
Ile Ile Thr Lys Val Val Glu Pro Lys Ile Lys Val Ile Glu Gly Ser
        675                 680                 685
Leu Gln Pro Ile Ile Lys Thr Glu Gly Pro Thr Leu Thr Lys Val Lys
    690                 695                 700
Ile Glu Gly Glu Pro Glu Phe Arg Leu Ile Lys Gly Glu Thr Ile
705                 710                 715                 720
Thr Glu Val Ile His Gly Glu Pro Ile Ile Lys Lys Tyr Thr Lys Ile
                725                 730                 735
Ile Asp Gly Val Pro Val Glu Ile Thr Glu Lys Glu Thr Arg Glu Glu
            740                 745                 750
Arg Ile Ile Thr Gly Pro Glu Ile Lys Tyr Thr Arg Ile Ser Thr Gly
        755                 760                 765
Gly Gly Glu Thr Glu Glu Thr Leu Lys Lys Leu Leu Gln Glu Glu Val
    770                 775                 780
Thr Lys Val Thr Lys Phe Ile Glu Gly Gly Asp Gly His Leu Phe Glu
785                 790                 795                 800
Asp Glu Glu Ile Lys Arg Leu Leu Gln Gly Asp Thr Pro Val Arg Lys
                805                 810                 815
Leu Gln Ala Asn Lys Lys Val Gln Gly Ser Arg Arg Leu Arg Glu
            820                 825                 830
Gly Arg Ser Gln
        835

<210> SEQ ID NO 3
<211> LENGTH: 2958
<212> TYPE: DNA
<213> ORGANISM: Homo sapiens
<220> FEATURE:
<221> NAME/KEY: CDS
<222> LOCATION: (12)..(2267)

<400> SEQUENCE: 3
agagactcaa g atg att ccc ttt tta ccc atg ttt tct cta cta ttg ctg      50
            Met Ile Pro Phe Leu Pro Met Phe Ser Leu Leu Leu Leu
              1               5                  10 ctt att gtt aac cct ata aac gcc aac aat cat tat gac aag atc ttg      98
Leu Ile Val Asn Pro Ile Asn Ala Asn Asn His Tyr Asp Lys Ile Leu
 15                  20                  25 gct cat agt cgt atc agg ggt cgg gac caa ggc cca aat gtc tgt gcc     146
Ala His Ser Arg Ile Arg Gly Arg Asp Gln Gly Pro Asn Val Cys Ala
 30                  35                  40                  45 ctt caa cag att ttg ggc acc aaa aag aaa tac ttc agc act tgt aag     194
Leu Gln Gln Ile Leu Gly Thr Lys Lys Lys Tyr Phe Ser Thr Cys Lys
                 50                  55                  60 aac tgg tat aaa aag tcc atc tgt gga cag aaa acg act gtt tta tat     242
Asn Trp Tyr Lys Lys Ser Ile Cys Gly Gln Lys Thr Thr Val Leu Tyr
             65                  70                  75 gaa tgt tgc cct ggt tat atg aga atg gaa gga atg aaa ggc tgc cca     290
Glu Cys Cys Pro Gly Tyr Met Arg Met Glu Gly Met Lys Gly Cys Pro
         80                  85                  90 gca gtt ttg ccc att gac cat gtt tat ggc act ctg ggc atc gtg gga     338
Ala Val Leu Pro Ile Asp His Val Tyr Gly Thr Leu Gly Ile Val Gly
     95                 100                 105 gcc acc aca acg cag cgc tat tct gac gcc tca aaa ctg agg gag gag     386
Ala Thr Thr Thr Gln Arg Tyr Ser Asp Ala Ser Lys Leu Arg Glu Glu
110                 115                 120                 125
```

-continued

| | |
|---|---|
| atc gag gga aag gga tcc ttc act tac ttt gca ccg agt aat gag gct<br>Ile Glu Gly Lys Gly Ser Phe Thr Tyr Phe Ala Pro Ser Asn Glu Ala<br>            130                  135                  140 | 434 |
| tgg gac aac ttg gat tct gat atc cgt aga ggt ttg gag agc aac gtg<br>Trp Asp Asn Leu Asp Ser Asp Ile Arg Arg Gly Leu Glu Ser Asn Val<br>                145                  150                  155 | 482 |
| aat gtt gaa tta ctg aat gct tta cat agt cac atg att aat aag aga<br>Asn Val Glu Leu Leu Asn Ala Leu His Ser His Met Ile Asn Lys Arg<br>           160                  165                  170 | 530 |
| atg ttg acc aag gac tta aaa aat ggc atg att att cct tca atg tat<br>Met Leu Thr Lys Asp Leu Lys Asn Gly Met Ile Ile Pro Ser Met Tyr<br>175                  180                  185 | 578 |
| aac aat ttg ggg ctt ttc att aac cat tat cct aat ggg gtt gtc act<br>Asn Asn Leu Gly Leu Phe Ile Asn His Tyr Pro Asn Gly Val Val Thr<br>190                  195                  200                  205 | 626 |
| gtt aat tgt gct cga atc atc cat ggg aac cag att gca aca aat ggt<br>Val Asn Cys Ala Arg Ile Ile His Gly Asn Gln Ile Ala Thr Asn Gly<br>                210                  215                  220 | 674 |
| gtt gtc cat gtc att gac cgt gtg ctt aca caa att ggt acc tca att<br>Val Val His Val Ile Asp Arg Val Leu Thr Gln Ile Gly Thr Ser Ile<br>           225                  230                  235 | 722 |
| caa gac ttc att gaa gca gaa gat gac ctt tca tct ttt aga gca gct<br>Gln Asp Phe Ile Glu Ala Glu Asp Asp Leu Ser Ser Phe Arg Ala Ala<br>        240                  245                  250 | 770 |
| gcc atc aca tcg gac ata ttg gag gcc ctt gga aga gac ggt cac ttc<br>Ala Ile Thr Ser Asp Ile Leu Glu Ala Leu Gly Arg Asp Gly His Phe<br>255                  260                  265 | 818 |
| aca ctc ttt gct ccc acc aat gag gct ttt gag aaa ctt cca cga ggt<br>Thr Leu Phe Ala Pro Thr Asn Glu Ala Phe Glu Lys Leu Pro Arg Gly<br>270                  275                  280                  285 | 866 |
| gtc cta gaa agg ttc atg gga gac aaa gtg gct tcc gaa gct ctt atg<br>Val Leu Glu Arg Phe Met Gly Asp Lys Val Ala Ser Glu Ala Leu Met<br>                290                  295                  300 | 914 |
| aag tac cac atc tta aat act ctc cag tgt tct gag tct att atg gga<br>Lys Tyr His Ile Leu Asn Thr Leu Gln Cys Ser Glu Ser Ile Met Gly<br>           305                  310                  315 | 962 |
| gga gca gtc ttt gag acg ctg gaa gga aat aca att gag ata gga tgt<br>Gly Ala Val Phe Glu Thr Leu Glu Gly Asn Thr Ile Glu Ile Gly Cys<br>        320                  325                  330 | 1010 |
| gac ggt gac agt ata aca gta aat gga atc aaa atg gtg aac aaa aag<br>Asp Gly Asp Ser Ile Thr Val Asn Gly Ile Lys Met Val Asn Lys Lys<br>335                  340                  345 | 1058 |
| gat att gtg aca aat aat ggt gtg atc cat ttg att gat cag gtc cta<br>Asp Ile Val Thr Asn Asn Gly Val Ile His Leu Ile Asp Gln Val Leu<br>350                  355                  360                  365 | 1106 |
| att cct gat tct gcc aaa caa gtt att gag ctg gct gga aaa cag caa<br>Ile Pro Asp Ser Ala Lys Gln Val Ile Glu Leu Ala Gly Lys Gln Gln<br>                370                  375                  380 | 1154 |
| acc acc ttc acg gat ctt gtg gcc caa tta ggc ttg gca tct gct ctg<br>Thr Thr Phe Thr Asp Leu Val Ala Gln Leu Gly Leu Ala Ser Ala Leu<br>                  385                  390                  395 | 1202 |
| agg cca gat gga gaa tac act ttg ctg gca cct gtg aat aat gca ttt<br>Arg Pro Asp Gly Glu Tyr Thr Leu Leu Ala Pro Val Asn Asn Ala Phe<br>        400                  405                  410 | 1250 |
| tct gat gat act ctc agc atg gtt cag cgc ctc ctt aaa tta att ctg<br>Ser Asp Asp Thr Leu Ser Met Val Gln Arg Leu Leu Lys Leu Ile Leu<br>415                  420                  425 | 1298 |
| cag aat cac ata ttg aaa gta aaa gtt ggc ctt aat gag ctt tac aac<br>Gln Asn His Ile Leu Lys Val Lys Val Gly Leu Asn Glu Leu Tyr Asn<br>430                  435                  440                  445 | 1346 |

```
ggg caa ata ctg gaa acc atc gga ggc aaa cag ctc aga gtc ttc gta      1394
Gly Gln Ile Leu Glu Thr Ile Gly Gly Lys Gln Leu Arg Val Phe Val
            450                 455                 460 tat cgt aca gct gtc tgc att gaa aat tca tgc atg gag aaa ggg agt      1442
Tyr Arg Thr Ala Val Cys Ile Glu Asn Ser Cys Met Glu Lys Gly Ser
                465                 470                 475 aag caa ggg aga aac ggt gcg att cac ata ttc cgc gag atc atc aag      1490
Lys Gln Gly Arg Asn Gly Ala Ile His Ile Phe Arg Glu Ile Ile Lys
        480                 485                 490 cca gca gag aaa tcc ctc cat gaa aag tta aaa caa gat aag cgc ttt      1538
Pro Ala Glu Lys Ser Leu His Glu Lys Leu Lys Gln Asp Lys Arg Phe
    495                 500                 505 agc acc ttc ctc agc cta ctt gaa gct gca gac ttg aaa gag ctc ctg      1586
Ser Thr Phe Leu Ser Leu Leu Glu Ala Ala Asp Leu Lys Glu Leu Leu
510                 515                 520                 525 aca caa cct gga gac tgg aca tta ttt gtg cca acc aat gat gct ttt      1634
Thr Gln Pro Gly Asp Trp Thr Leu Phe Val Pro Thr Asn Asp Ala Phe
                530                 535                 540 aag gga atg act agt gaa gaa aaa gaa att ctg ata cgg gac aaa aat      1682
Lys Gly Met Thr Ser Glu Glu Lys Glu Ile Leu Ile Arg Asp Lys Asn
            545                 550                 555 gct ctt caa aac atc att ctt tat cac ctg aca cca gga gtt ttc att      1730
Ala Leu Gln Asn Ile Ile Leu Tyr His Leu Thr Pro Gly Val Phe Ile
        560                 565                 570 gga aaa gga ttt gaa cct ggt gtt act aac att tta aag acc aca caa      1778
Gly Lys Gly Phe Glu Pro Gly Val Thr Asn Ile Leu Lys Thr Thr Gln
    575                 580                 585 gga agc aaa atc ttt ctg aaa gaa gta aat gat aca ctt ctg gtg aat      1826
Gly Ser Lys Ile Phe Leu Lys Glu Val Asn Asp Thr Leu Leu Val Asn
590                 595                 600                 605 gaa ttg aaa tca aaa gaa tct gac atc atg aca aca aat ggt gta att      1874
Glu Leu Lys Ser Lys Glu Ser Asp Ile Met Thr Thr Asn Gly Val Ile
                610                 615                 620 cat gtt gta gat aaa ctc ctc tat cca gca gac aca cct gtt gga aat      1922
His Val Val Asp Lys Leu Leu Tyr Pro Ala Asp Thr Pro Val Gly Asn
            625                 630                 635 gat caa ctg ctg gaa ata ctt aat aaa tta atc aaa tac atc caa att      1970
Asp Gln Leu Leu Glu Ile Leu Asn Lys Leu Ile Lys Tyr Ile Gln Ile
        640                 645                 650 aag ttt gtt cgt ggt agc acc ttc aaa gaa atc ccc gtg act gtc tat      2018
Lys Phe Val Arg Gly Ser Thr Phe Lys Glu Ile Pro Val Thr Val Tyr
    655                 660                 665 aag cca att att aaa aaa tac acc aaa atc att gat gga gtg cct gtg      2066
Lys Pro Ile Ile Lys Lys Tyr Thr Lys Ile Ile Asp Gly Val Pro Val
670                 675                 680                 685 gaa ata act gaa aaa gag aca cga gaa gaa cga atc att aca ggt cct      2114
Glu Ile Thr Glu Lys Glu Thr Arg Glu Glu Arg Ile Ile Thr Gly Pro
                690                 695                 700 gaa ata aaa tac act agg att tct act gga ggt gga gaa aca gaa gaa      2162
Glu Ile Lys Tyr Thr Arg Ile Ser Thr Gly Gly Gly Glu Thr Glu Glu
            705                 710                 715 act ctg aag aaa ttg tta caa gaa gac aca ccc gtg agg aag ttg caa      2210
Thr Leu Lys Lys Leu Leu Gln Glu Asp Thr Pro Val Arg Lys Leu Gln
        720                 725                 730 gcc aac aaa aaa gtt caa ggt tct aga aga cga tta agg gaa ggt cgt      2258
Ala Asn Lys Lys Val Gln Gly Ser Arg Arg Arg Leu Arg Glu Gly Arg
    735                 740                 745 tct cag tga aaatccaaaa accagaaaaa aatgtttata caaccctaag              2307
Ser Gln
```

-continued

```
750
tcaataacct gaccttagaa aattgtgaga gccaagttga cttcaggaac tgaaacatca    2367
gcacaaagaa gcaatcatca ataattctg aacacaaatt taatatttt ttttctgaat     2427 gagaaacatg agggaaattg tggagttagc ctcctgtggt aaaggaattg aagaaaatat   2487
aacaccttac acccttttc atcttgacat taaaagttct ggctaacttt ggaatccatt    2547
agagaaaaat ccttgtcacc agattcatta caattcaaat cgaagagttg tgaactgtta   2607
tcccattgaa aagaccgagc cttgtatgta tgttatggat acataaaatg cacgcaagcc   2667
attatctctc catgggaagc taagttataa aaataggtgc ttggtgtaca aaacttttta   2727
tatcaaaagg ctttgcacat ttctatatga gtgggtttac tggtaaatta tgttattttt   2787
tacaactaat tttgtactct cagaatgttt gtcatatgct tcttgcaatg catatttttt   2847
aatctcaaac gtttcaataa aaccattttt cagatataaa gagaattact tcaaattgag   2907
taattcagaa aaactcaaga tttaagttaa aaagtggttt ggacttggga a             2958
```

<210> SEQ ID NO 4
<211> LENGTH: 751
<212> TYPE: PRT
<213> ORGANISM: Homo sapiens

<400> SEQUENCE: 4

```
Met Ile Pro Phe Leu Pro Met Phe Ser Leu Leu Leu Leu Leu Ile Val
  1               5                  10                  15

Asn Pro Ile Asn Ala Asn Asn His Tyr Asp Lys Ile Leu Ala His Ser
                 20                  25                  30

Arg Ile Arg Gly Arg Asp Gln Gly Pro Asn Val Cys Ala Leu Gln Gln
             35                  40                  45

Ile Leu Gly Thr Lys Lys Lys Tyr Phe Ser Thr Cys Lys Asn Trp Tyr
         50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255
```

-continued

```
Ser Asp Ile Leu Glu Ala Leu Gly Arg Asp Gly His Phe Thr Leu Phe
        260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
        340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
                420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
        530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
        610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
        660                 665                 670
```

```
Ile Lys Lys Tyr Thr Lys Ile Ile Asp Gly Val Pro Val Glu Ile Thr
            675                 680                 685

Glu Lys Glu Thr Arg Glu Glu Arg Ile Ile Thr Gly Pro Glu Ile Lys
    690                 695                 700

Tyr Thr Arg Ile Ser Thr Gly Gly Glu Thr Glu Thr Leu Lys
705                 710                 715                 720

Lys Leu Leu Gln Glu Asp Thr Pro Val Arg Lys Leu Gln Ala Asn Lys
            725                 730                 735

Lys Val Gln Gly Ser Arg Arg Leu Arg Glu Gly Arg Ser Gln
            740                 745                 750

<210> SEQ ID NO 5
<211> LENGTH: 2360
<212> TYPE: DNA
<213> ORGANISM: Homo sapiens
<220> FEATURE:
<221> NAME/KEY: CDS
<222> LOCATION: (12)..(2360)

<400> SEQUENCE: 5
agagactcaa g atg att ccc ttt tta ccc atg ttt tct cta cta ttg ctg      50
           Met Ile Pro Phe Leu Pro Met Phe Ser Leu Leu Leu Leu
             1               5                  10 ctt att gtt aac cct ata aac gcc aac aat cat tat gac aag atc ttg      98
Leu Ile Val Asn Pro Ile Asn Ala Asn Asn His Tyr Asp Lys Ile Leu
 15              20                  25 gct cat agt cgt atc agg ggt cgg gac caa ggc cca aat gtc tgt gcc     146
Ala His Ser Arg Ile Arg Gly Arg Asp Gln Gly Pro Asn Val Cys Ala
30              35                  40                  45 ctt caa cag att ttg ggc acc aaa aag aaa tac ttc agc act tgt aag     194
Leu Gln Gln Ile Leu Gly Thr Lys Lys Lys Tyr Phe Ser Thr Cys Lys
                50                  55                  60 aac tgg tat aaa aag tcc atc tgt gga cag aaa acg act gtg tta tat     242
Asn Trp Tyr Lys Lys Ser Ile Cys Gly Gln Lys Thr Thr Val Leu Tyr
            65                  70                  75 gaa tgt tgc cct ggt tat atg aga atg gaa gga atg aaa ggc tgc cca     290
Glu Cys Cys Pro Gly Tyr Met Arg Met Glu Gly Met Lys Gly Cys Pro
        80                  85                  90 gca gtt ttg ccc att gac cat gtt tat ggc act ctg ggc atc gtg gga     338
Ala Val Leu Pro Ile Asp His Val Tyr Gly Thr Leu Gly Ile Val Gly
    95                  100                 105 gcc aca aca acg cag cgc tat tct gac gcc tca aaa ctg agg gag gag     386
Ala Thr Thr Thr Gln Arg Tyr Ser Asp Ala Ser Lys Leu Arg Glu Glu
110                 115                 120                 125 atc gag gga aag gga tcc ttc act tac ttt gca ccg agt aat gag gct     434
Ile Glu Gly Lys Gly Ser Phe Thr Tyr Phe Ala Pro Ser Asn Glu Ala
                130                 135                 140 tgg gac aac ttg gat tct gat atc cgt aga ggt ttg gag agc aac gtg     482
Trp Asp Asn Leu Asp Ser Asp Ile Arg Arg Gly Leu Glu Ser Asn Val
            145                 150                 155 aat gtt gaa tta ctg aat gct tta cat agt cac atg att aat aag aga     530
Asn Val Glu Leu Leu Asn Ala Leu His Ser His Met Ile Asn Lys Arg
        160                 165                 170 atg ttg acc aag gac tta aaa aat ggc atg att att cct tca atg tat     578
Met Leu Thr Lys Asp Leu Lys Asn Gly Met Ile Ile Pro Ser Met Tyr
    175                 180                 185 aac aat ttg ggg ctt ttc att aac cat tat cct aat ggg gtt gtc act     626
Asn Asn Leu Gly Leu Phe Ile Asn His Tyr Pro Asn Gly Val Val Thr
190                 195                 200                 205 gtt aat tgt gct cga atc atc cat ggg aac cag att gca aca aat ggt     674
Val Asn Cys Ala Arg Ile Ile His Gly Asn Gln Ile Ala Thr Asn Gly
```

```
                Val Asn Cys Ala Arg Ile Ile His Gly Asn Gln Ile Ala Thr Asn Gly
                                    210                 215                 220 gtt gtc cat gtc att gac cgt gtg ctt aca caa att ggt acc tca att                 722
Val Val His Val Ile Asp Arg Val Leu Thr Gln Ile Gly Thr Ser Ile
            225                 230                 235 caa gac ttc att gaa gca gaa gat gac ctt tca tct ttt aga gca gct                 770
Gln Asp Phe Ile Glu Ala Glu Asp Asp Leu Ser Ser Phe Arg Ala Ala
        240                 245                 250 gcc atc aca tcg gac ata ttg gag gcc ctt gga aga gac ggt cac ttc                 818
Ala Ile Thr Ser Asp Ile Leu Glu Ala Leu Gly Arg Asp Gly His Phe
    255                 260                 265 aca ctc ttt gct ccc acc aat gag gct ttt gag aaa ctt cca cga ggt                 866
Thr Leu Phe Ala Pro Thr Asn Glu Ala Phe Glu Lys Leu Pro Arg Gly
270                 275                 280                 285 gtc cta gaa agg atc atg gga gac aaa gtg gct tcc gaa gct ctt atg                 914
Val Leu Glu Arg Ile Met Gly Asp Lys Val Ala Ser Glu Ala Leu Met
                290                 295                 300 aag tac cac atc tta aat act ctc cag tgt tct gag tct att atg gga                 962
Lys Tyr His Ile Leu Asn Thr Leu Gln Cys Ser Glu Ser Ile Met Gly
            305                 310                 315 gga gca gtc ttt gag acg ctg gaa gga aat aca att gag ata gga tgt                1010
Gly Ala Val Phe Glu Thr Leu Glu Gly Asn Thr Ile Glu Ile Gly Cys
        320                 325                 330 gac ggt gac agt ata aca gta aat gga atc aaa atg gtg aac aaa aag                1058
Asp Gly Asp Ser Ile Thr Val Asn Gly Ile Lys Met Val Asn Lys Lys
    335                 340                 345 gat att gtg aca aat aat ggt gtg atc cat ttg att gat cag gtc cta                1106
Asp Ile Val Thr Asn Asn Gly Val Ile His Leu Ile Asp Gln Val Leu
350                 355                 360                 365 att cct gat tct gcc aaa caa gtt att gag ctg gct gga aaa cag caa                1154
Ile Pro Asp Ser Ala Lys Gln Val Ile Glu Leu Ala Gly Lys Gln Gln
                370                 375                 380 acc acc ttc acg gat ctt gtg gcc caa tta ggc ttg gca tct gct ctg                1202
Thr Thr Phe Thr Asp Leu Val Ala Gln Leu Gly Leu Ala Ser Ala Leu
            385                 390                 395 agg cca gat gga gaa tac act ttg ctg gca cct gtg aat aat gca ttt                1250
Arg Pro Asp Gly Glu Tyr Thr Leu Leu Ala Pro Val Asn Asn Ala Phe
        400                 405                 410 tct gat gat act ctc agc atg gat cag cgc ctc ctt aaa tta att ctg                1298
Ser Asp Asp Thr Leu Ser Met Asp Gln Arg Leu Leu Lys Leu Ile Leu
    415                 420                 425 cag aat cac ata ttg aaa gta aaa gtt ggc ctt aat gag ctt tac aac                1346
Gln Asn His Ile Leu Lys Val Lys Val Gly Leu Asn Glu Leu Tyr Asn
430                 435                 440                 445 ggg caa ata ctg gaa acc atc gga ggc aaa cag ctc aga gtc ttc gta                1394
Gly Gln Ile Leu Glu Thr Ile Gly Gly Lys Gln Leu Arg Val Phe Val
                450                 455                 460 tat cgt aca gct gtc tgc att gaa aat tca tgc atg gag aaa ggg agt                1442
Tyr Arg Thr Ala Val Cys Ile Glu Asn Ser Cys Met Glu Lys Gly Ser
            465                 470                 475 aag caa ggg aga aac ggt gcg att cac ata ttc cgc gag atc atc aag                1490
Lys Gln Gly Arg Asn Gly Ala Ile His Ile Phe Arg Glu Ile Ile Lys
        480                 485                 490 cca gca gag aaa tcc ctc cat gaa aag tta aaa caa gat aag cgc ttt                1538
Pro Ala Glu Lys Ser Leu His Glu Lys Leu Lys Gln Asp Lys Arg Phe
    495                 500                 505
```

```
agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525 aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530                 535                 540 aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555 gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570 gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585 gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590                 595                 600                 605 gaa ttg aaa tca aaa gaa tct gac atc atg aca aca aat ggt gta att     1874
Glu Leu Lys Ser Lys Glu Ser Asp Ile Met Thr Thr Asn Gly Val Ile
                610                 615                 620 cat gtt gta gat aaa ctc ctc tat cca gca gac aca cct gtt gga aat     1922
His Val Val Asp Lys Leu Leu Tyr Pro Ala Asp Thr Pro Val Gly Asn
            625                 630                 635 gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650 aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665 aga ccc aca cta aca aaa gtc aaa att gaa ggt gaa cct gaa ttc aga     2066
Arg Pro Thr Leu Thr Lys Val Lys Ile Glu Gly Glu Pro Glu Phe Arg
670                 675                 680                 685 ctg att aaa gaa ggt gaa aca ata act gaa gtg atc cat gga gag cca     2114
Leu Ile Lys Glu Gly Glu Thr Ile Thr Glu Val Ile His Gly Glu Pro
                690                 695                 700 att att aaa aaa tac acc aaa atc att gat gga gtg cct gtg gaa ata     2162
Ile Ile Lys Lys Tyr Thr Lys Ile Ile Asp Gly Val Pro Val Glu Ile
            705                 710                 715 act gaa aaa gag aca cga gaa gaa cga atc att aca ggt cct gaa ata     2210
Thr Glu Lys Glu Thr Arg Glu Glu Arg Ile Ile Thr Gly Pro Glu Ile
        720                 725                 730 aaa tac act agg att tct act gga ggt gga gaa aca gaa gaa act ctg     2258
Lys Tyr Thr Arg Ile Ser Thr Gly Gly Gly Glu Thr Glu Glu Thr Leu
    735                 740                 745 aag aaa ttg tta caa gaa gaa gac aca ccc gtg agg aag ttg caa gcc     2306
Lys Lys Leu Leu Gln Glu Glu Asp Thr Pro Val Arg Lys Leu Gln Ala
750                 755                 760                 765 aac aaa aaa gtt caa gga tct aga aga cga tta agg gaa ggt cgt tct     2354
Asn Lys Lys Val Gln Gly Ser Arg Arg Arg Leu Arg Glu Gly Arg Ser
                770                 775                 780 cag tga                                                              2360
Gln

<210> SEQ ID NO 6
<211> LENGTH: 782
<212> TYPE: PRT
<213> ORGANISM: Homo sapiens

<400> SEQUENCE: 6
```

```
Met Ile Pro Phe Leu Pro Met Phe Ser Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65              70                  75                  80

Pro Gly Tyr Met Arg Met Glu Gly Met Lys Gly Cys Pro Ala Val Leu
            85                  90                  95

Pro Ile Asp His Val Tyr Gly Thr Leu Gly Ile Val Gly Ala Thr Thr
        100                 105                 110

Thr Gln Arg Tyr Ser Asp Ala Ser Lys Leu Arg Glu Glu Ile Glu Gly
    115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415
```

-continued

```
Thr Leu Ser Met Asp Gln Arg Leu Leu Lys Leu Ile Leu Gln Asn His
            420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Leu Thr Gln Pro
        515                 520                 525
Gly Asp Trp Thr Leu Phe Val Pro Thr Asn Asp Ala Phe Lys Gly Met
    530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
        595                 600                 605
Ser Lys Glu Ser Asp Ile Met Thr Thr Asn Gly Val Ile His Val Val
    610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Ser Thr Phe Lys Glu Ile Pro Val Thr Val Tyr Arg Pro Thr
            660                 665                 670
Leu Thr Lys Val Lys Ile Glu Gly Glu Pro Glu Phe Arg Leu Ile Lys
        675                 680                 685
Glu Gly Glu Thr Ile Thr Glu Val Ile His Gly Glu Pro Ile Ile Lys
    690                 695                 700
Lys Tyr Thr Lys Ile Ile Asp Gly Val Pro Val Glu Ile Thr Glu Lys
705                 710                 715                 720
Glu Thr Arg Glu Glu Arg Ile Ile Thr Gly Pro Glu Ile Lys Tyr Thr
                725                 730                 735
Arg Ile Ser Thr Gly Gly Gly Glu Thr Glu Glu Thr Leu Lys Lys Leu
            740                 745                 750
Leu Gln Glu Glu Asp Thr Pro Val Arg Lys Leu Gln Ala Asn Lys Lys
        755                 760                 765
Val Gln Gly Ser Arg Arg Arg Leu Arg Glu Gly Arg Ser Gln
    770                 775                 780
```